(12) United States Patent
Latham et al.

(10) Patent No.: US 12,139,755 B2
(45) Date of Patent: Nov. 12, 2024

(54) METHODS OF RNA AMPLIFICATION

(71) Applicant: ASURAGEN, INC., Austin, TX (US)

(72) Inventors: Gary J. Latham, Austin, TX (US); Richard Andrew Blidner, Austin, TX (US); Liangjing Chen, Austin, TX (US)

(73) Assignee: ASURAGEN, INC., Austin, TX (US)

( * ) Notice: Subject to any disclaimer, the term of this patent is extended or adjusted under 35 U.S.C. 154(b) by 275 days.

(21) Appl. No.: 17/556,387

(22) Filed: Dec. 20, 2021

(65) Prior Publication Data

US 2022/0177949 A1 Jun. 9, 2022

Related U.S. Application Data

(63) Continuation of application No. 16/478,705, filed as application No. PCT/US2018/013830 on Jan. 16, 2018, now Pat. No. 11,236,384.

(60) Provisional application No. 62/448,371, filed on Jan. 19, 2017.

(51) Int. Cl.
| | | |
|---|---|---|
| *C12Q 1/68* | (2018.01) | |
| *C12N 9/12* | (2006.01) | |
| *C12Q 1/6844* | (2018.01) | |
| *C12Q 1/686* | (2018.01) | |

(52) U.S. Cl.
CPC ............ *C12Q 1/686* (2013.01); *C12N 9/1276* (2013.01); *C12Q 1/6846* (2013.01); *C12Q 2521/107* (2013.01); *C12Q 2527/125* (2013.01); *C12Q 2531/101* (2013.01)

(58) Field of Classification Search
CPC ............................ C12Q 1/686; C12Q 1/6846; C12Q 2521/107; C12Q 2527/125; C12Q 2531/101; C12N 9/1276
See application file for complete search history.

(56) References Cited

U.S. PATENT DOCUMENTS

| | | |
|---|---|---|
| 5,310,652 A | 5/1994 | Gelfand et al. |
| 2003/0228616 A1 | 12/2003 | Arezi et al. |
| 2010/0209970 A1 | 8/2010 | Latham |

FOREIGN PATENT DOCUMENTS

| | | |
|---|---|---|
| WO | WO 91/09944 A2 | 7/1991 |
| WO | WO 98/44161 A1 | 10/1998 |
| WO | WO 2003/025132 A2 | 3/2003 |
| WO | WO 2004/024749 A2 | 3/2004 |

OTHER PUBLICATIONS

Heller et al., (2019) "Engineering of a thermostable viral polymerase using metagenome-derived diversity for highly sensitive and specific RT-PCR", Nucleic Acids Research, 47(7):3619-30.

(Continued)

*Primary Examiner* — Jezia Riley

(74) *Attorney, Agent, or Firm* — FINNEGAN, HENDERSON, FARABOW, GARRETT & DUNNER, LLP

(57) ABSTRACT

The invention relates to methods of RNA amplification, including methods for the reverse transcription of cDNA from RNA using a thermostable reverse transcriptase. In a particular aspect, the methods are capable of linear amplification of an RNA template through multiple cycles of cDNA synthesis.

23 Claims, 2 Drawing Sheets

Specification includes a Sequence Listing.

(56) References Cited

OTHER PUBLICATIONS

International Patent Application No. PCT/US2018/013830, filed Jan. 16, 2018, by Asuragen, Inc.: International Search Report and Written Opinion, mailed May 24, 2018 (15 pages).
Sano et al., (2011) "Mutations to create thermostable reverse transcriptase with bacterial family a DNA polymerase from Thermotoga petrophila K4", Journal of Bioscience and Bioengineering, 113(3):315-21.
Schonbrunner et al., (2006) "Chimeric Thermostable DNA Polymerases with Reverse Transcriptase and Attenuated 3'-5' Exonuclease Activity", Biochemistry, 45(42), pp. 12786-12795.
Moser, M.J. et al., (2012) "Thermostable DNA Polymerase from a Viral Metagenome is a Potent RT-PCR Enzyme", PLOS One, vol. 7, Issue 6, pp. 1-13.
Dube, S., (1997) "Fun Facts for DNA Electrophoresis", Focus, vol. 19, No. 3, pp. 1-2.
PyroScript RT-PCR Master Mix Kit, (2010) pp. 1-7.
PyroPhage ™ 3173 DNA Polymerase, (2007) pp. 1-10.
Shum, J. et al., (2009) "Hot Start PCR Update: CleanAmp™ Primers", Glen Research, vol. 21, pp. 1-20.
Lehman, U. et al., (2001) "Real-Time PCR Analysis of DNA and RNA extracted from Formalin-Fixed and Paraffin-Embedded Biopsies", Methods, vol. 25, pp. 409-418.
HawkZ05 Fast Polymerase, Roche CustomBiotech, (2016) pp. 1-2.

METHODS OF RNA AMPLIFICATION

This application is a continuation of application Ser. No. 16/478,705, filed Jul. 17, 2019, which is a national stage application under 35 U.S.C. § 371 of PCT/US2018/13830, filed Jan. 16, 2018, which claims the benefit of priority of U.S. Provisional Application No. 62/448,371, filed Jan. 19, 2017, which are incorporated herein by reference.

The present application contains a Sequence Listing which has been submitted electronically in ASCII format and is hereby incorporated by reference in its entirety. Said ASCII copy, created on Dec. 23, 2019, is named 10256_0054-00000_SL.txt and is 2,194 bytes in size.

BACKGROUND

Methods to amplify RNA are important for diagnostic purposes. Cellular mRNA represents gene expression activity at a defined time. Gene expression is affected by cell cycle progression, developmental regulation, disease state, or response to internal and external stimuli. The profile of expressed genes for any cell type in an organism reflects normal or disease states, response to various stimuli, developmental stages, or cell differentiation. Non-coding RNAs have been shown to be of great importance in regulation of various cellular functions and in certain disease pathologies. Diagnostically relevant RNAs are often present at very low levels. Thus, amplification methods capable of detecting low copy number RNAs are important.

Current methods of RNA amplification include the reverse transcriptase-polymerase chain reaction (RT-PCR) method and variations thereof. These methods first copy RNA by reverse transcription to form a single stranded DNA complementary to the RNA (cDNA, or so-called first-strand cDNA), which is followed by polymerase chain reaction (PCR) amplification of the cDNA to provide multiple copies.

Commonly used reverse transcriptases, such as those from Moloney Murine Leukemia Virus (MMLV), are mesophilic and, as such, have optimal activity at moderate temperature regimes such as 37° C.-42° C. In some cases, these reverse transcriptases have been modified to confer greater thermostability at temperatures of 60°-70° C. but rarely higher. In other cases, DNA polymerases with native thermostability have been found to manifest reverse transcriptase activity, particular when standard reaction conditions are altered using unconventional components such as $Mn^{2+}$ ions instead of $Mg^{2+}$ ion. However, these enzymes may manifest inferior cDNA synthesis compared to dedicated reverse transcriptase enzymes, and the addition of $Mn^{2+}$ can accelerate the hydrolysis of RNA at high reaction temperatures (see, AbouHaidar and Ivanov, Z. Naturforsch C. 54(7-8):542-548 (1999)).

Reagent stability and activity, including nonenzymatic RNA hydrolysis, creates a barrier to amplification of RNA via thermocycling reactions. While native thermostable DNA polymerases have been engineered to have reverse transcriptase activity, such enzymes were largely envisioned as useful in single-enzyme reverse transcriptase-polymerase chain reaction methods that comprise a single, extended length reverse transcription step at moderate temperature, followed by repeated cDNA amplification steps, e.g., via PCR, that include high denaturation temperatures.

BRIEF DESCRIPTION OF DRAWINGS

The drawings are not necessarily to scale or exhaustive. Instead, emphasis is generally placed upon illustrating the principles of the inventions described herein. The accompanying drawings, which are incorporated in and constitute a part of this specification, illustrate several embodiments consistent with the disclosure and, together with the description, serve to explain the principles of the disclosure. In the drawings.

DETAILED DESCRIPTION OF THE EMBODIMENTS

Figure 1:
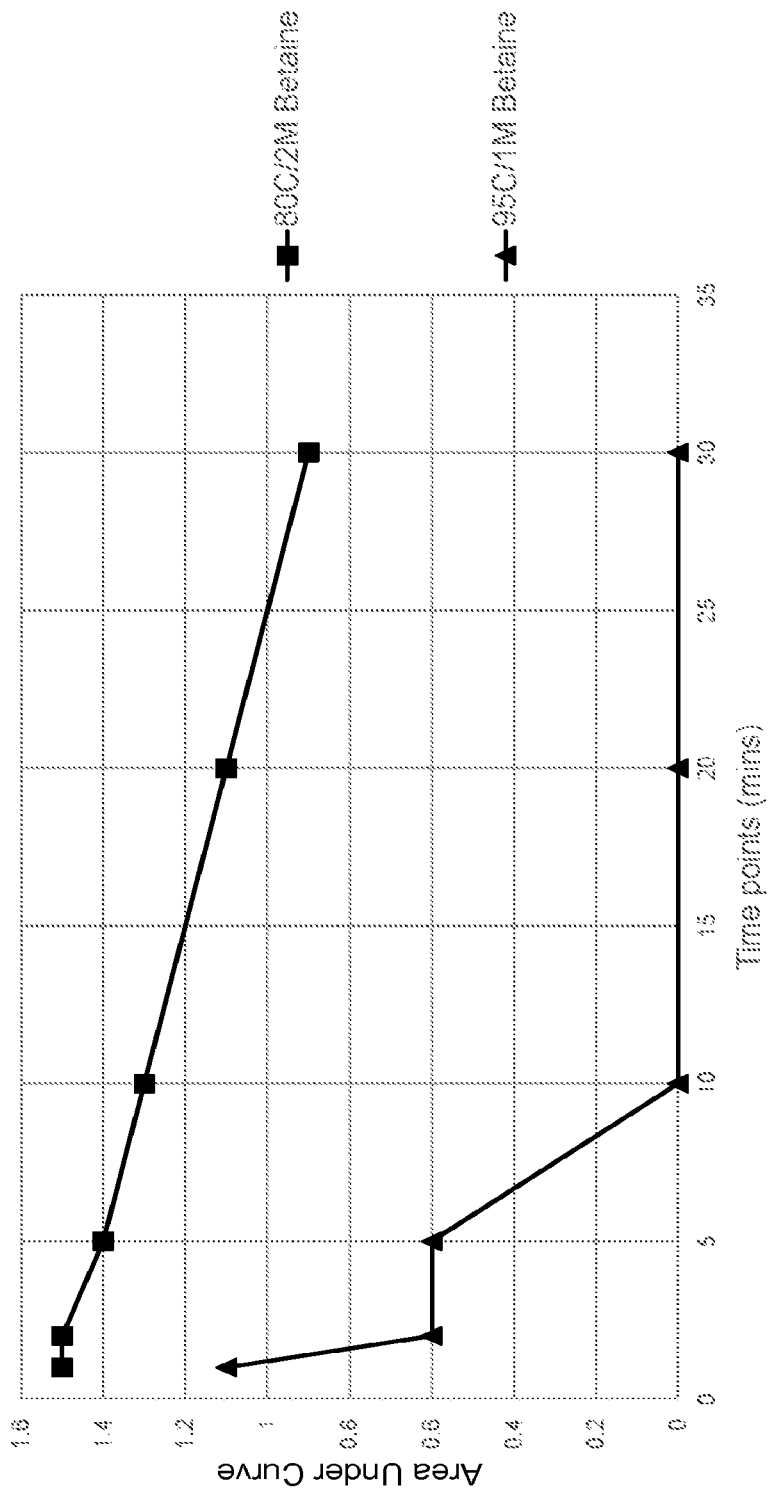
FIG. 1 Depicts the peak area (for the expected RNA) from the bioanalyzer results for the exposure of 80° C./2M Betaine and 95° C./1M Betaine for 1, 2, 5, 10, 20, 30 mins. Results were plotted for the relative peak area for each measurement. By directly measuring the remaining intact RNA after heat exposure in Buffer A, appreciably reduced RNA fragmentation at 2M Betaine/80° C. compared to 1M Betaine/95° C. was observed.

The invention relates to methods for RNA amplification, including methods for reverse transcribing nucleic acid molecules. More specifically, the invention relates to improving the synthesis of complementary DNA (cDNA) from RNA, e.g., a target RNA such as a messenger RNA (mRNA) using a thermostable reverse transcriptase.

The specification is most thoroughly understood in light of the teachings of the references cited within the specification. The embodiments within the specification provide an illustration of embodiments of the invention and should not be construed to limit the scope of the invention. One of skill in the art readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Unless otherwise indicated, the terms "at least", "less than", "about" or similar terms preceding a series of elements or a range are to be understood to refer to every element in the series or range. Those skilled in the art will recognize, or be able to ascertain using no more than routine experimentation, many equivalents to the specific embodiments of the invention described herein. Such equivalents are intended to be encompassed by the following claims.

"Polymerase chain reaction" and "PCR" refer interchangeably to a DNA synthesis reaction in which the reaction mixture is subjected to at least two complete reaction cycles, each reaction cycle comprising a denaturation period and at least one annealing and/or extension period, resulting if successful in synthesis of copies of a DNA template in at least the initial cycles, and copies of the copies in at least the later cycles, generally resulting in amplification of the template.

"RNA" refers to ribonucleic acid, a biopolymeric chain of predominantly ribonucleotide residues linked generally by phosphodiester bonds. "DNA" refers to deoxyribonucleic acid, a biopolymeric chain of predominantly deoxyribonucleotide residues linked generally by phosphodiester bonds. "Complementary DNA" and "cDNA" are used interchangeably to refer to a synthetic DNA that is reverse transcribed from RNA using a reverse transcriptase enzyme. cDNA may be single-stranded in the form of first-strand cDNA or first-strand cDNA hybridized to template RNA, or double-stranded, e.g., after a complementary strand is synthesized using the first-strand cDNA as a template. In some embodiments, the cDNA comprises a sequence that is substantially identical to a part of the RNA template or its complement.

As used herein, "dNTP" refers to deoxynucleotide triphosphate, e.g., dATP, dCTP, dGTP, dTTP, dUTP, and analogs thereof. As used herein, "nucleotide analogs" are molecules or ions comprising a base moiety other than the natural bases adenine (A), cytosine (C), guanine (G), thymine (T), or uracil (U), a sugar moiety identical or similar to deoxyribose, and at least one phosphate or multiple phosphate (e.g., diphosphate or triphosphate) moiety. The nucleotide analog is an analog of a specific nucleotide, in particular dATP, dCTP, dGTP, dTTP, or dUTP, when it comprises a triphosphate and a sugar moiety, the structure and configuration of both of which are suitable for incorporation into a nucleic acid double helix by a polymerase, and a base whose base pairing properties in a nucleic acid double helix and loci of incorporation by DNA polymerases in a nucleic acid double helix are most similar to one of the five previously listed nucleotides, with the exception that analogs of dTTP will generally also be analogs of dUTP and vice versa.

The term "analog" used in conjunction with terms including but not limited to "nucleoside", "base", "nucleobase", or "residue" is to be interpreted in the same manner as if it were used in conjunction with "nucleotide."

As used herein, a "polynucleotide polymerase" refers to an enzyme that catalyzes the polymerization of nucleotides. Generally, synthesis begins at the 3' end of a primer sequence annealed to a polynucleotide template strand and moves to the 5' end of the template strand. The polymerization of ribonucleotides to synthesize RNA is catalyzed by RNA polymerase. The polymerization of deoxynucleotides to synthesize DNA is catalyzed by DNA polymerase. A DNA polymerase may be a DNA polymerase that synthesizes DNA from an RNA template, e.g., a reverse transcriptase. A reverse transcriptase may be RNA-dependent. A reverse transcriptase may synthesize DNA from RNA and DNA templates, or it may be capable of synthesizing DNA from RNA and DNA templates.

A. Reverse Transcriptase

The methods of the invention comprise using a reverse transcriptase to synthetize DNA from RNA. As used herein, a "reverse transcriptase" refers to an enzyme capable of synthesizing a DNA strand, e.g., cDNA, using an RNA strand, e.g., mRNA, as a template. Many naturally occurring reverse transcriptases use a primer to synthesize DNA from an RNA template. In some embodiments, reverse transcription is a DNA polymerase that performs both reverse transcription and DNA amplification. In some embodiments, the reverse transcriptase is a thermostable reverse transcriptase that has detectable reverse transcriptase activity at or above about 75° C. In some embodiments, the reverse transcriptase is an error-correcting reverse transcriptase. In some embodiments, the reverse transcriptase comprises at least one proofreading domain, such as a 3' to 5' exonuclease domain. In some embodiments, the reverse transcriptase does not comprise a functional proofreading domain, such as a 3' to 5' exonuclease domain.

A reverse transcriptase may be natural or synthetic, e.g., modified or engineered. In some embodiments, the reverse transcriptase is selected from a retroviral reverse transcriptase, a family A DNA polymerase with reverse transcriptase activity, a family B DNA polymerase with reverse transcriptase activity, or modified, mutated, and/or engineered variations thereof. In some embodiments, the reverse transcriptase may be a viral, eukaryotic, or prokaryotic reverse transcriptase, including engineered versions of the same. In some embodiments, the reverse transcriptase is selected from OmniAmp™ (Lucigen), an RTX polymerase, Hawk-Z05® (Roche), Hawk-Z05® Fast (Roche), KOD, Maxima™ Reverse Transcriptase (ThermoFisher), Maxima™ H Minus Reverse Transcriptase (ThermoFisher), an MMLV reverse transcriptase derivative or engineered polymerase, MonsterScript™ (Epicentre), Pyrophage® (Lucigen), RocketScript™ RT (Bioneer), SunScript® reverse transcriptase RNase H-(Sygnis), SunScript® reverse transcriptase RNase H+ (Sygnis), Superscript™ IV (ThermoFisher), a Superscript™ IV derivative, Taq, TGIRT™-III enzyme (InGex), ThermoScript™ RT (ThermoFisher), Tth (Promega and others), Volcano2G® DNA polymerase (MyPOLS Biotech), and WarmStart® RTx Reverse Transcriptase (NEB). See, e.g., Myers and Gelfand, Biochemistry, 6; 30(31): 7661-7666 (1991); Moser et al., PLOS One., 7(6):e383712012 (2012); Chander et al., Front Microbiol., 1(5):395 (2014); Ellefson et al., Science., 24; 352(6293): 1590-1593 (2016) (disclosing various KOD polymerase variants, called "RTX", including RTX exo-); U.S. Pat. Nos. 5,674,738; 6,127,155; 7,179,590; 8,093,030; 8,753,845; WO2011135280A2; and WO2013156786A1. The disclosure of reverse transcriptase enzymes in each of these references is specifically incorporated by reference. In some embodiments, the reverse transcriptase is selected from OmniAmp™ and Hawk-Z05. In some embodiments, the reverse transcriptase is selected from an RTX polymerase of Ellefson et al., Science., 24; 352(6293): 1590-1593 (2016). In some embodiments, the reverse transcriptase is an RTX polymerase. In some embodiments, the reverse transcriptase is OmniAmp™. In some embodiments, the reverse transcriptase is RTX or variants such as B11, an engineered form of KOD DNA polymerase that includes up to 37 amino acid changes, and particularly mutations at R97, Y384, V389, E664, G711, and E735, or RTX exo-, an identical or similar enzyme composition with an additional mutation or mutations that inactivate the 3'-5' exonuclease activity, such as N210D. In some embodiments, the reverse transcriptase is Hawk-Z05®. In some embodiments, the reverse transcriptase is capable of synthesizing multiple copies of first-strand, single-stranded cDNA from an RNA template. In some embodiments, the reverse transcriptase is capable of multiple cycles of cDNA synthesis, e.g., in a thermocycling apparatus. In methods claimed herein, the reverse transcriptase is a thermostable reverse transcriptase. In some embodiments, the reverse transcriptase lacks a 3'-5' exonuclease activity, an RNAse activity, and/or a strand displacement activity.

B. RNA Template and RNA Preparation

An RNA template is a sequence of RNA present in a sample that is the target of synthesis in a reaction catalyzed by a reverse transcriptase. In some embodiments, the RNA template is rRNA, tRNA, mRNA, siRNA, shRNA, miRNA, snoRNA, primary transcript RNA, or synthetic RNA. In some embodiments, the RNA template is mRNA. In some embodiments, the RNA template is a low-abundance RNA. In some embodiments, the RNA template is a disease-associated RNA. In some embodiments, the RNA template is an oncogene RNA. The size of the RNA template may be about 20, 25, 50, 75, 100, 200, 300, 500, or 700 bp, or 1, 1.5, 2, 2.5, 3, 4, 5, 7, or 10 kb. The size of the RNA template may be between 50 bp and 10 kb, 50 bp and 500 bp, 60 bp and 500 bp, 50 bp and 1 kb, 50 bp and 5 kb, 100 bp and 10 kb, 100 bp and 1 kb, 200 bp and 10 kb, 300 bp and 10 kb, 500 bp and 10 kb, 700 bp and 10 kb, 1 kb and 10 kb, 1.5 kb and 10 kb, 2 kb and 10 kb, 3 kb and 10 kb, 4 kb and 10 kb, 5 kb and 10 kb.

In some embodiments, the RNA template is isolated from a cell culture or a tissue sample. In some embodiments, the tissue sample is a fresh tissue sample, a fine-needle aspiration (FNA) biopsy, a frozen tissue sample, a fresh frozen tissue sample, a biofluid tissue sample, a paraffin-embedded and fixed tissue sample, or a formalin-fixed paraffin-embedded (FFPE) tissue sample. In some embodiments, the tissue sample is a solid tissue sample. In additional embodiments, the tissue sample is a biofluid sample. Advantageously, in some embodiments, the methods describes herein may be used to detect and analyze low-abundance RNA, e.g., RNA from a solid tissue sample or a biofluid sample. Exemplary biofluid samples useful for methods described herein include blood, serum, plasma, amniotic fluid, cerebrospinal fluid, interstitial fluid, lymph, pleural fluid, saliva, fine needle aspiration, or urine.

In some embodiments, the RNA template is in a complex RNA sample. In certain embodiments, a cellular RNA sample is used. In other embodiments, a total RNA sample is used. In certain embodiments, the RNA sample is obtained from a tissue sample. In still further embodiments, the RNA sample is obtained from a cell culture.

General methods for RNA extraction are known in the art. See, e.g., Ausubel et al., Current Protocols of Molecular Biology, John Wiley and Sons (1997). RNA may be extracted from paraffin embedded tissues. See, e.g., Rupp and Locker, Lab Invest. 56:A67 (1987); De Andrés et al., BioTechniques 18:42044 (1995). RNA may be extracted from cultured cells and tissue samples using a commercial purification kit according to the manufacturer's instructions, e.g., using Qiagen RNeasy mini-columns, MasterPure™ Complete DNA Kit, EPICENTRE® RNA Purification Kit, and Ambion, Inc., Paraffin Block RNA Isolation Kit, Tel-Test RNA Stat-60. In certain embodiments, the extracted RNA is an RNA sample or an isolated RNA sample.

C. Reverse Transcription Polymerase Chain Reaction (RT-PCR)

In some embodiments, the sample containing the RNA template described above is subjected to reverse transcription to produce cDNA from the RNA template, followed by amplification from the cDNA in a PCR reaction ("RT-PCR"). "Reverse transcription" refers to a process by which cDNA is synthetized from RNA, e.g., using a reverse transcriptase.

In some embodiments, the RT-PCR is a one-step RT-PCR. For example, one-step RT-PCR may use the reverse transcriptase activity of DNA polymerases from thermophilic organisms, which are active at high temperatures (see, Myers and Gelfand, Biochemistry, 6; 30(31):7661-7666 (1991)). In brief, a one-step RT-PCR reaction comprises mixing an RNA template with at least one reverse transcriptase and incubating the mixture under conditions sufficient to synthesize and amplify a cDNA molecule that is complementary to all or part of the template.

In some embodiments, the RT-PCR is a multi-step RT-PCR. In some embodiments, the RT-PCR is a two-step RT-PCR. In brief, a two-step RT-PCR reaction comprises mixing an RNA template with at least one reverse transcriptase, incubating the mixture under conditions sufficient generate a cDNA molecule that is complementary to all or part of the template, mixing the cDNA molecule with at least one DNA polymerase, and incubating the cDNA mixture under conditions sufficient to amplify the nucleic acid molecule. One-step and multi-step RT-PCR methods are known in the art.

D. Amplification of cDNA

The RNA amplification methods optionally include a cDNA amplification step that amplifies DNA copies of the RNA template, such as PCR amplification. The phrase "cDNA amplification", as used herein, refers to synthesis from a cDNA template. Additional methods of amplification of DNA are also contemplated. In some embodiments, suitable methods for amplifying the repeat region to generate amplification products include polymerase chain reaction (PCR), real-time PCR (RT-PCR), nucleic acid sequence-base amplification (NASBA), ligase chain reaction, multiplex ligatable probe amplification, invader technology (Third Wave), rolling circle amplification, in vitro transcription, strand displacement amplification, transcription-mediated amplification (TMA), RNA (e.g., Eberwine) amplification, loop-mediated isothermal amplification, or any other methods that are known to one of skill in the art.

E. Methods

In some embodiments, the RNA amplification methods unexpectedly yield robust linear amplification in a cDNA synthesis step, despite well-documented evidence that RNA suffers metal-activated hydrolysis at high temperatures, such as temperatures required to denature RNA:cDNA hybrids. The observation of RNA amplification in reaction conditions that contain $Mn^{2+}$ ions rather than $Mg^{2+}$ is particularly surprising given the greater effect of $Mn^{2+}$ in degrading RNA at elevated temperatures. See, Myers and Gelfand, Biochemistry, 6; 30(31):7661-7666 (1991); Ausubel et al., Current Protocols of Molecular Biology, John Wiley and Sons (1997).

The terms "reverse transcription" and "cDNA synthesis" are used herein to refer to first-strand cDNA synthesis from an RNA template, unless otherwise specified. In some embodiments, the RNA amplification methods unexpectedly yield >100% cDNA synthesis. In some embodiments, a cDNA synthesis step unexpectedly yields >100% cDNA synthesis. Reverse transcription cycling conditions can demonstrate product generation that is consistent with exponential amplification, which is nonspecific and minimized in the methods claimed herein. In some embodiments, linear amplification during a cDNA synthesis step is achieved at unexpectedly low denaturation temperatures, for example 75° C. or 80° C., which can eliminate product generation consistent with exponential amplification. In some embodiments, the RNA amplification methods unexpectedly yield >200% cDNA synthesis, >500% cDNA synthesis, or >1000% cDNA synthesis. Previous studies have shown that RT cycling would be contraindicated, because the elevated temperatures needed to denature RNA:cDNA hybrids would promote metal-activated hydrolysis of RNA and reduce the length of cDNA and/or the sensitivity of RNA detection. See, Myers and Gelfand, 1991. In addition, polymerases previously identified with sufficient thermostability to support denaturation of RNA:cDNA at conventional denaturation templates, for example 98° C., and thus cycling of the RNA template for additional rounds of first-strand cDNA synthesis have been historically limited to those with relatively poor reverse transcriptase activity that further require non-native divalent metal ions, such as $Mn^{2+}$, as cofactors. The inventors have discovered RNA amplification reaction conditions that allow thermocycling during the reverse transcriptase phase of the methods, while minimizing degradation of and priming by the RNA template or derivatives or fragments thereof. In some embodiments, the methods increase analytical sensitivity to detect and quantify low-level RNA variants or low-abundance RNAs. In some embodiments, the methods improve precision to detect and quantify low-level variants or low-abundance RNAs. In some embodiments, the methods improve robustness to detect and quantify variants or low abundance RNAs. In further embodiments, the methods improve read-through of highly structured RNAs during cDNA synthesis cycling. In additional embodiments, the methods provide streamlined workflows using one-step, one-tube RT-PCR with RT cycling.

In some embodiments, the RNA amplification method includes a cDNA synthesis step that produces a ratio of cDNA to RNA template that is greater than 1:1. In some embodiments, the RNA amplification method or a cDNA synthesis step produces a ratio of cDNA to RNA template that is greater than about 2:1. In some embodiments, the ratio of cDNA to RNA template is greater than about 3:1. In some embodiments, the ratio of cDNA to RNA template is greater than about 5:1. In some embodiments, the ratio of cDNA to RNA template is greater than about 10:1. In some embodiments, the ratio of cDNA to RNA template is greater than about 20:1. In some embodiments, the ratio of cDNA to RNA template is greater than about 40:1. In some embodiments, the ratio of cDNA to RNA template is greater than about 50:1. In some embodiments, the ratio of cDNA to RNA template is about 2:1 to 100:1.

In some embodiments, the RNA amplification method comprises a reverse transcriptase. In some embodiments, the RNA amplification method comprises a thermostable reverse transcriptase. In some embodiments, the RNA amplification method comprises a reverse transcriptase and another DNA polymerase. In some embodiments, copy number analysis of the reverse transcription products may be analyzed using PCR, e.g., digital PCR (ddPCR) or real-time PCR or quantitative PCR (qPCR).

In some embodiments, the RNA amplification method comprises contacting an RNA template with a thermostable reverse transcriptase and a first primer complementary to the RNA template; performing linear amplification of the RNA template that includes at least two cycles of cDNA synthesis primed by the first primer in a reaction volume, and amplifying the cDNA in the reaction volume. In certain embodiments, the cycle of cDNA synthesis includes an extension temperature and a denaturation temperature, and wherein the denaturation temperature is between about 75° C. to 98° C.

In some embodiments, the RNA amplification method comprises contacting an RNA template from a biological sample with a thermostable reverse transcriptase and a first primer complementary to the RNA template in a reaction volume; performing linear amplification of the RNA template in the reaction volume to produce cDNA; and amplifying the cDNA in the reaction volume using at least a second primer in the reaction volume. In certain embodiments, the linear amplification comprises at least two cycles between an extension temperature and a denaturation temperature, and wherein the denaturation temperature is between about 75° C. to 98° C.

In some embodiments, the RNA amplification method comprises contacting an RNA template with a thermostable reverse transcriptase and a first primer complementary to the RNA template; synthesizing cDNA through at least 2 cycles between an extension temperature and a denaturation temperature of between about 75° C. to 90° C. in a reaction volume comprising 1-3M betaine; and producing >100% conversion of the RNA template to a cDNA copy of the RNA template.

In some embodiments, the RNA amplification method comprises contacting the RNA template with a thermostable reverse transcriptase in a reaction volume containing buffer, dNTPs, and a first primer complementary to the RNA template; producing a cDNA from the RNA template in the reaction volume; denaturing the cDNA:RNA template duplex; repeating steps the cDNA synthesis and denaturation step; and producing a ratio of cDNA to RNA template of greater than or about 2 to 1.

In some embodiments, the cDNA synthesis step does not comprise a functional primer complementary to the cDNA. In some embodiments, the reaction volume does not comprise a functional primer complementary to the cDNA. In some embodiments, the reaction volume does not comprise a functional primer capable of amplifying the cDNA.

In some embodiments, a functional second primer complementary to the cDNA is subsequently included in the reaction volume (after cDNA synthesis) in order to amplify the cDNA. In some embodiments, the reaction volume comprises a nonfunctional second primer that is complementary to the cDNA and that can be functionalized to enable amplification of the cDNA. A nonfunctional primer, in this context, is a primer that is present during first-strand cDNA synthesis and is complementary to a sequence present in the newly-synthesized cDNA, but is incapable of supporting the production of second strand cDNA.

F. Design of Primers

PCR primers can be designed based upon exon, intron, or intergenic sequences present in the RNA of interest, for example present in an RNA transcript of interest. In some embodiments, the RNA amplification methods are primed using at least one primer complementary to the RNA template. In some embodiments, the RNA amplification methods are primed using specific primers, random primers, and/or oligo-dT primers. In some embodiments, the primer is a DNA primer. In alternate embodiments, the primer is an RNA primer. In some embodiments, an RNA primer can be extended using dNTP's and/or a DNA template to generate a chimeric product.

In certain embodiments, the RNA amplification reactions may include non-specific RNA amplification. In certain embodiments, the RNA amplification reactions do not include significant non-specific RNA amplification. In some embodiments, e.g., at higher temperatures or cycle numbers of amplification, degraded and fragmented RNA can itself be used as an RNA primer. During a cDNA synthesis step, such a reaction is called non-specific cDNA synthesis. RNA degradation may be caused by using temperatures as high as 98° C. and/or high cycle numbers, particularly in the presence of divalent metal ions, which may cause degradation, e.g., metal-activated hydrolysis. RNA hydrolysis may be analyzed by methods known in the art, e.g., gel electrophoresis, Agilent 2100 Bioanalyzer, capillary electrophoresis, chip electrophoresis, and digital electropherograms. In some embodiments, an RNA primer is favored for particular amplification conditions.

As used herein, the term "primer" refers to nucleic acid molecules and derivatives thereof that are added to the RNA amplification methods and that start a nucleic acid synthesis reaction. The primers may be designed to anneal to the about 6-45, 6-30, 15-30, 15-25, 15-20, 20-30, 20-25, 15-45, 20-45, or 30-45 nucleotides at each end of the template sequence. Primers and probes can be designed using publicly available software, e.g., DNA BLAT (Kent, Genome Res. 12(4):656-64 (2002)), BLAST, Primer Express (Applied Biosystems), MGB assay-by-design (Applied Biosystems), Primer3 (Rozen and Skaletsky (2000), Rrawetz S, Misener S (eds) Bioinformatics Methods and Protocols: Methods in Molecular Biology. Humana Press, Totowa, NJ, pp 365-386), and variations thereof.

Other factors that can influence primer design include primer length, melting temperature (Tm), and G/C content, specificity, complementary primer sequences, and 3'-end sequence. In general, optimal primers are generally 15-45 bases in length, and contain about 25-75% G+C bases, and exhibit a melting temperature between 50-70° C. See also, Dieffenbach et al, "General Concepts for PCR Primer Design" in: PCR Primer, A Laboratory Manual, Cold Spring Harbor Laboratory Press, New York, 1995, pp. 133-155; Innis and Gelfand, "Optimization of PCRs" in: PCR Protocols, A Guide to Methods and Applications, CRC Press, London, 1994, pp. 5-11; and Plasterer, T. N. Primerselect: Primer and probe design. Methods Mol. Biol. 70:520-527 (1997), the entire disclosures of which are hereby expressly incorporated by reference.

In some embodiments, only one or more reverse, i.e., antisense, primers is used for reverse transcription, e.g. cDNA synthesis, and the reaction in generally unidirectional. In these embodiments, primarily antisense copies of the antisense template are generated. In some embodiments, a reverse primer is not used.

In some embodiments, a non-functional second primer (e.g. sense primer) is included in the RNA amplification method, e.g. during cDNA synthesis. In some embodiments, at least 1, 2, 3, 4, 5, or more non-functional reverse primers or forward primers are included in the RNA amplification method, e.g. during cDNA synthesis. In some embodiments, at least 1, 2, 3, 4, 5, or more functional reverse primers or forward primers are included in the cDNA amplification step of the RNA amplification method. In certain embodiments, a reverse primer is used for a cDNA synthesis step, and functional forward and reverse primers are included in a cDNA amplification step.

G. Linear Amplification

In some embodiments, the cDNA synthesis stage (also called first-strand cDNA synthesis) during RNA amplification is linear, and the subsequent stage of RNA amplification is exponential. In some embodiments, the RNA amplification methods comprise a linear amplification step that includes at least two cycles of cDNA synthesis. In "linear amplification", as used herein, the amount of cDNA produced is about or approximately proportional to the number of cycles performed. In some embodiments, the cDNA synthesis is linear for at least 5 cycles. In some embodiments, the cDNA synthesis is linear for at least 10 cycles. In some embodiments, the cDNA synthesis is linear for at least 20 cycles. In some embodiments, the cDNA synthesis is linear for at least 30 cycles. In some embodiments, the cDNA synthesis is linear for at least 40 cycles. In some embodiments, the cDNA synthesis amplification is linear for up to or about 30, 25, 20, 15, 10, 9, 8, 7, 6, or 5 cycles. Linear amplification of the RNA template or linear cDNA synthesis is determined by quantitating amplification/synthesis using a single primer complementary to the template over 2-50 or more cycles, and determining whether the amount of cDNA produced is proportional to the number of cycles performed.

Assays to measure linear amplification include those that allow for quantification of the cDNA produced during the RT step, such as qPCR, as a function of the number of RT cycles performed. In a standard PCR reaction (using forward and reverse primers), amplification of a template is non-linear. In one embodiment, linear amplification during cDNA synthesis is measured as set forth in Example 1. In some embodiments, at higher cycle numbers, e.g., above 2, 5, or 10 cycles, the amplification during cDNA synthesis is greater than proportional, e.g. exponential amplification. In some embodiments, at higher cycle numbers, e.g., above 2, 5, or 10 cycles, the amplification during cDNA synthesis is less than proportional, e.g. cDNA synthesis plateaus, for example because of saturation.

H. Reaction Conditions and Cycling

In some embodiments, the reaction conditions and the cycling protocol is optimized to extend the window for linear amplification, e.g., by protecting against RNA degradation, protecting the enzyme from inactivation, and/or reducing the cDNA:RNA denaturation temperature. In certain aspects, the methods include reduced concentrations of divalent metal cations. In certain aspects, the methods include reduced thermal cycling times at the denaturation stage. In some embodiments, a denaturation time during cycling is 0.1, 0.25, 0.5, 0.75, 1, 1.5, 2, 2.5, 3, 4, or 5 minutes. In some embodiments, an extension time during cycling is 0.1, 0.25, 0.5, 0.75, 1, 1.5, 2, 2.5, 3, 4, 5, or minutes. In additional embodiments, reaction volume includes at least one adjuvant to reduce the cDNA:RNA denaturation temperature.

In some embodiments, the RNA amplification method comprises at least 2 cycles of cDNA synthesis. In some embodiments, the RNA amplification method comprises 2-60 cycles of cDNA synthesis. In some embodiments, the RNA amplification method comprises 2-50 cycles of cDNA synthesis. In some embodiments, the RNA amplification method comprises 5-50 cycles of cDNA synthesis. In some embodiments, the RNA amplification method comprises 10-50 cycles of cDNA synthesis. In some embodiments, the RNA amplification method comprises 20-50 cycles of cDNA synthesis. In some embodiments, the RNA amplification method comprises 2-100 cycles of cDNA synthesis. In some embodiments, the RNA amplification method comprises 5-100 cycles of cDNA synthesis. In some embodiments, the RNA amplification method comprises 10-100 cycles of cDNA synthesis. In some embodiments, the RNA amplification method comprises 20-100 cycles of cDNA synthesis. In some embodiments, the RNA amplification method comprises 20-60 cycles of cDNA synthesis.

In some embodiments, a particular denaturation temperature is used in the reaction to extend the window for linear amplification. In some embodiments, the denaturation temperature is between about 75° C.-98° C. The denaturation temperature may be applied for a denaturation time, for example the denaturation temperature may be applied for about 15 seconds, 30 seconds, or 45 seconds in a cycle. In some embodiments, the denaturation temperature is between about 75° C.-98° C. In some embodiments, the denaturation temperature is selected from about or is about 75° C., 80° C., 85° C., 90° C., 95° C. and 98° C. In some embodiments, the denaturation temperature is selected from about 75° C.-80° C., 80° C.-85° C., 85° C.-90° C., and 90° C.-98° C. In some embodiments, the denaturation temperature is about 75° C.-85° C. In some embodiments, the denaturation temperature is about 80° C.-98° C. In some embodiments, the denaturation temperature is about 80° C.-90° C. In some embodiments, the denaturation temperature is about 80° C.-85° C. Extension temperatures are known in the art for various reverse transcriptases, including thermostable reverse transcriptase. In some embodiments, an extension temperature is about 55° C.

In some embodiments, an adjuvant is used in the reaction to extend the window for linear amplification. In some embodiments, at least one adjuvant may be included in the RNA amplification reaction in order to increase yield, specificity, and/or consistency. In some embodiments, at least one adjuvant may be included in the RNA amplification reaction in order to lower the Tm of a double-stranded template. In some embodiments, the adjuvant is a "melting temperature adjuvant" in that it lowers the Tm of a double-stranded or partially double stranded nucleic acid template. "Tm" is the temperature at which 50% by mass of a given nucleic acid sample or primer-template complex in a given solution is single-stranded, and 50% by mass is double-stranded. Adjuvants may function through helix destabilization, neutralization of reaction inhibitors, or other mechanisms, including unknown mechanisms.

Adjuvants include, but are not limited to, betaine (N,N, N-trimethylglycine), betaine analogs, glycerol, bovine serum albumin (BSA), polyethylene glycol, ammonium-based ions, tetramethylammonium chloride, tetramethylammonium, 7-deaza-GTP, neutral detergents, dimethylsulfoxide (DMSO), methanol, ethanol, isopropanol, formamide, acetone, acetamide, N-methylformamide, N,N-dimethylformamide, acetone, acetimide, N-methylacetimide, N,N-dimethylacetimide, 2-pyrrolidone, N-methylpyrrolidone, propionamide, and isobutyramide. Neutral detergents include, but are not limited to, TWEEN-20 (polyethylene glycol sorbitan monolaurate, CAS number 9005-64-5), β-octyl-glucoside, Octyl-β-Thio-glucopyranoside, Triton X-100, Triton X-114, NP-40, Brij-35, Brij-58, Tween-80, Pluronic F-68, Pluronic F-127, Deoxy Big CHAP, CHAPS, CHES, nonyl phenoxylpolyethoxylethanol (Tergitol-type NP-40), and octyl phenoxylpolyethoxylethanol (Igepal CA-630). Betaine analogs include, without limitation, homodeanol betaine, deanol betaine, propio betaine, homoglycerol betaine, diethanol homobetaine, triethanol homobetaine, hydroxypropyl homobetaine, N-Methyl-N-(2-carboxyethyl) morpholinium inner salt, N-Methyl-N-(2-carboxyethyl)piperidinium inner salt, N-Methyl-N-(2-carboxyethyl)pyrrolidinium inner salt, N,N-dimethyl-N-(2-hydroxyethyl)-N-(2-sulfoethyl)ammonium inner salt, N,N-dimethyl-N-(2-hydroxyethyl)-N-(3-sulfopropyl)ammonium inner salt, N,N-dihydroxyethyl-N-methyl-N-(3-sulfopropyl)ammonium inner salt, N,N-dimethyl-N-(2-hydroxyethyl)-N-(4-sulfobutyl)ammonium inner salt, N-methyl-N-(3-sulfopropyl)morpholinium inner salt, and N-methyl-N-(3-sulfopropyl)piperidium inner salt. In certain embodiments, the melting temperature adjuvant is chosen from betaine, a betaine analog, and DMSO. In some embodiments, the melting temperature adjuvant is betaine. In some embodiments, the melting temperature adjuvant is a betaine analog. In some embodiments, the melting temperature adjuvant is DMSO.

A "betaine analog" is any neutral chemical compound with a positively charged cationic functional group which bears no hydrogen atom, e.g., an ammonium ion or phosphonium ion, and with a negatively charged functional group such as a carboxylate group which may not be adjacent to the cationic site. The invention may relate to the use of betaine analogs with molecular weights less than or equal to 600 Da; less than or equal to 300 Da; between 75 and 600 Da; or between 75 and 300 Da. The invention may additionally or alternatively relate to the use of betaine analogs that comprise an ammonium moiety and/or a carboxylate moiety.

Betaine, betaine analogs and/or other adjuvants may be provided at molar concentrations between 0.01 and 5 M, 0.01 and 4 M, 0.01 and 3 M, 0.01 and 2.5 M, 0.1 and 5 M, 0.1 and 4 M, 0.1 and 3 M, 0.1 and 2.5 M, 0.5 and 3 M, 1 and 3 M, 1.5 and 3 M, 2 and 3 M, 2.5 and 3 M, 0.5 and 5 M, 0.7 and 5 M, 1 and 5 M, 1.5 and 5 M, 2 and 5 M, 0.5 and 4 M, 1 and 2.5 M, or 1.5 and 2.5 M, for example, about 0.01, 0.02, 0.05, 0.1, 0.2, 0.5, 0.75, 1, 1.25, 1.5, 1.6, 1.7, 1.8, 1.9, 2.0, 2.1, 2.2, 2.3, 2.4, 2.5, 2.6, 2.7, 2.8, 2.9, 3, 3.5, 4, 4.5, or 5 M. Alternatively, adjuvants may be provided at w/v or v/v percentage concentrations of between 0.1 and 50%, 0.2 and 50%, 0.5 and 50%, 1 and 50%, 2 and 50%, 5 and 50%, 0.1 and 40%, 0.1 and 30%, 0.1 and 20%, 0.5 and 40%, 1 and 30%, or 2 and 20%, for example, about 0.1, 0.2, 0.5, 1, 2, 5, 10, 15, 20, 25, 30, 35, 40, 45, or 50% by volume. Neutral detergents may be provided at between 0.0001 and 10% by volume, 0.0002 and 10%, 0.0005 and 10%, 0.001 and 10%, 0.002 and 10%, 0.005 and 10%, 0.01 and 10%, 0.02 and 10%, 0.05 and 10%, 0.0001 and 5%, 0.0001 and 2%, 0.0001 and 1%, 0.0005 and 1%, or 0.001 and 1%, e.g., about 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10% by volume. One of skill in the art will recognize appropriate concentrations for various adjuvants.

In some embodiments, the adjuvant is betaine. In some embodiments, the RNA amplification method comprises at least or about 1M betaine. In some embodiments, the RNA amplification method comprises at least or about 1-3M betaine. In some embodiments, the RNA amplification method comprises at least or about 2-2.5M betaine. In some embodiments, the RNA amplification method comprises at least or about 2M betaine. In some embodiments, the RNA amplification method comprises at least or about 2.5M betaine. In some embodiments, the adjuvant is polyethylene glycol.

In some embodiments, the RNA amplification methods include a lower denaturation temperature, e.g., less than about 98° C., when coupled with a higher betaine concentration, e.g., 1M, 1.5M, 2M, or 2.5M or higher. In some embodiments, the RNA amplification methods include a lower denaturation temperature, e.g., about 80°, 85°, or 90° C., when coupled with a higher betaine concentration, e.g., 1M, 1.5M, 2M, or 2.5M or higher In some embodiments, the RNA amplification methods include about 10 cDNA synthesis cycles using high concentrations of betaine, e.g., 1M, 1.5M, 2M, or 2.5M or higher, at a denaturation temperature of about 85° C. In some embodiments, the RNA amplification methods include about 20 cDNA synthesis cycles using high concentrations of betaine, e.g., 1M, 1.5M, 2M, or 2.5M or higher, at an even lower denaturation temperature, e.g., about 80° C.

In some embodiments, greater sensitivity and high specificity may be achieved at high cycle numbers, e.g., 10-20 cycles of cDNA synthesis, when coupled with a high betaine concentration, e.g., 1M, 1.5M, 2M, or 2.5M or higher.

In some embodiments, at a lower denaturation temperature, e.g., about 80° C. or 85° C., and a high betaine concentration, e.g., about 2M or 2.5M, exponential amplification is not observed even at 30 cycles of cDNA synthesis.

I. Divalent Metal Ions

In some embodiments, higher levels of reverse transcription activity can be achieved using a divalent metal ion, e.g., $Mg^{2+}$, $Mn^{2+}$, or $Co^{2+}$ or $Zn^{2+}$. In some embodiments, the reaction comprises $Mg^{2+}$. In some embodiments, the reaction comprises $Mn^{2+}$. In some embodiments, the reaction comprises use of a divalent metal ion whose concentration is higher than the total dNTP concentration. In some embodiments, the divalent metal ion concentration is less than or about 5 times the total dNTP concentration. In some embodiments, the divalent metal ion concentration is less than or about 2 times the total dNTP concentration. In some embodiments, a particular reverse transcriptase achieves higher levels of reverse transcription activity in combination with a particular divalent metal ion.

The divalent metal ion may be provided as a salt that contains the metal ion and the conjugate base of an acid. Magnesium salts may comprise, e.g., magnesium chloride, magnesium acetate, magnesium sulfate, magnesium bromide, or magnesium iodide. Manganese salts may comprise, e.g., manganese chloride, manganese acetate, manganese sulfate, manganese bromide, or manganese iodide. In some embodiments, particular reverse transcriptases are preferentially paired with particular cations. For example, Omni-Amp™ is paired with $Mg^{2+}$ in some embodiments. In certain embodiments, HawkZ05® is paired with $Mn^{2+}$.

Suitable concentrations of $Mg^{2+}$ or $Mn^{2+}$ are dependent on the total dNTP concentration (for example, where approximately 1 divalent ion is bound by approximately 1 dNTP molecule). Generally, total [dNTP] is 0.4-2 mM and the preferred [divalent ion] is 0.5-5 mM is suitable. Higher nominal concentrations of divalent ions may be used if chelators such as EDTA are included in the reaction. In some embodiments, magnesium salts are provided in such quantity that the final concentration of $Mg^{2+}$ may be between about 0.2 and 20 mM. In some embodiments, manganese salts are provided in such quantity that the final concentration of $Mn^{2+}$ may be between about 0.2 and 20 mM.

In some embodiments, the concentration of $Mg^{2+}$ is between about 0.5 and 10 mM, 0.5 and 9 mM, 0.5 and 8 mM, 0.5 and 7 mM, 0.5 and 6 mM, 0.5 and 5 mM, 0.5 and 4 mM, 0.5 and 3 mM, or 0.5 and 2 mM. In some embodiments, the concentration of $Mg^{2+}$ is between about 1 and 10 mM, 1 and 9 mM, 1 and 8 mM, 1 and 7 mM, 1 and 6 mM, 1 and 5 mM, 1 and 4 mM, 1 and 3 mM, or 1 and 2 mM. In some embodiments, the concentration of $Mg^{2+}$ is between about 1 and 5 mM, 2 and 5 mM, 3 and 5 mM, or 2 and 4 mM. In some embodiments, the concentration of $Mg^{2+}$ is between about 5 and 10 mM, 6 and 10 mM, 7 and 10 mM, 8 and 10 mM, or 9 and 10 mM. In some embodiments, the concentration of $Mg^{2+}$ is about 1 mM. In some embodiments, the concentration of $Mg^{2+}$ is about 5 mM. In some embodiments, the concentration of $Mg^{2+}$ is about 8 mM. In some embodiments, concentration of $Mg^{2+}$ is about 10 mM.

In some embodiments, the concentration of $Mn^{2+}$ is between about 0.5 and 10 mM, 0.5 and 9 mM, 0.5 and 8 mM, 0.5 and 7 mM, 0.5 and 6 mM, 0.5 and 5 mM, 0.5 and 4 mM, 0.5 and 3 mM, or 0.5 and 2 mM. In some embodiments, the concentration of $Mn^{2+}$ is between about 1 and 10 mM, 1 and 9 mM, 1 and 8 mM, 1 and 7 mM, 1 and 6 mM, 1 and 5 mM, 1 and 4 mM, 1 and 3 mM, or 1 and 2 mM. In some embodiments, the concentration of $Mn^{2+}$ is between about 1 and 5 mM, 2 and 5 mM, 3 and 5 mM, or 2 and 4 mM. In some embodiments, the concentration of $Mn^{2+}$ is between about 5 and 10 mM, 6 and 10 mM, 7 and 10 mM, 8 and 10 mM, or 9 and 10 mM. In some embodiments, the concentration of $Mn^{2+}$ is about 1 mM. In some embodiments, the concentration of $Mn^{2+}$ is about 5 mM. In some embodiments, the concentration of $Mn^{2+}$ is about 8 mM. In some embodiments, concentration of $Mn^{2+}$ is about 10 mM.

J. Reaction Conditions

A skilled person would optimize buffer, divalent cation, and K+ or other ion concentrations for each polymerase using information specific to the polymerase. In certain embodiments, cycling conditions are optimized. In some embodiments, a particular reverse transcriptase achieves higher levels of reverse transcription activity when used with a particular divalent metal ion. In some embodiments, the reverse transcriptase performs linear amplification better using manganese than magnesium. In alternate embodiments, the reverse transcriptase performs linear amplification better using magnesium than manganese.

In some embodiments, a reverse transcriptase capable of rapid cDNA synthesis is used. In some embodiments, a reverse transcriptase that can synthesize DNA with a reduced Km for dNTPs is used, allowing lower dNTP concentration to be used. In additional embodiments, the reaction is at a reduced pH that stabilizes RNA, such as approximately pH 4-5. In certain aspects, a polymerase that is robust to sample-specific inhibitors is used, allowing the methods to achieve linear amplification without formal RNA purification.

EXAMPLES

The following examples serve to illustrate, and in no way limit, the present disclosure.

Example 1: Reverse Transcriptase Cycling of Thermostable Polymerase Enzymes

Polymerase enzymes, PyroPhage® 3173 DNA Polymerase Wild Type (WT) (Lucigen Corp, Catalog No. 30051-1), OmniAmp™ DNA Polymerase (Lucigen Corp, Catalog No. 30065-1), and Tth DNA polymerase (Promega Corp, Part No. M210A) were tested for their ability to synthesize multiple single stranded cDNA from RNA template at four different RT cycle counts (1, 5, 10, and 20) using a mixture of MET Mutant (exon 14 skipped, that is, exon 13-15 variant) cell line RNA and wild type cell line TNA (containing RNA and DNA). The reactions for PyroPhage®, OmniAmp™ and Tth were 10 μL reactions and set up in accordance with their respective manufacturing protocols.

The reactions for Pyrophage® 3173 DNA Polymerase were set up in PyroPhage® 3173 PCR Buffer (final concentration: 20 mM Tris-HCl, 10 mM (NH4)2SO$_4$, 10 mM KCl, 2 mM MgSO4, 0.1% Triton X-100, thermoprotectant, pH 8.8 at 25° C.), dNTPs at a final concentration of 200 μM each (800 μM total), 1 μM reverse primer and 0.5 U of enzyme per 10 μL reaction. The RT reactions for OmniAmp™ enzyme were set up using DNA Polymerase Buffer C, dNTPs at final concentration of 800 μM each (3.2 mM total), Betaine at 0.15M final concentration, 1 μM reverse primer and 1× OmniAmp™ DNA Polymerase. The Buffer C contained MgSO$_4$ at 2 mM final concentration, however, the protocol recommended supplementation of MgSO$_4$ for efficient amplification by OmniAmp™. Therefore, an additional 8 mM MgSO$_4$ was added to reach a final concentration of 10 mM in the reactions. Other components of Buffer C were not disclosed by the supplier. In reactions with the Tth enzyme, the final concentration of components of Tth RT Buffer was 10 mM Tris-HCl, pH 8.3, 90 mM KCl, dNTPs at 200 μM each (800 μM total), 1 μM reverse primer, 0.5 U of enzyme per 10 μL reaction and MnCl$_2$ at a final concentration of 1 mM.

The RT cycling conditions were one cycle of 68° C./1 min, 55° C./1 min and 68° C./2 mins followed by 0, 4, 9 or 19 cycles of 95° C./15 secs, 55° C./1 min and 68° C./2 mins to achieve 1, 5,10 or 20 cycles of linear amplification. Copy number analysis of 20% of the RT product was assessed using in-house digital PCR (ddPCR™, QX200™ Droplet Digital PCR System) assays for MET exon 14 skipping (mutant MET) and wild type MET. Since only the reverse (antisense) primer was used for the RT, the reaction was intended to be unidirectional and only antisense copies of the original template were expected.

The reverse primer for RT cycling has the sequence of TACTGCACTTGTCGGCATGAA (SEQ ID NO: 1). The mutant MET exon 13-15 fusion detection uses the probe/primer pair sequence of/56-FAM/AG CAA ATT A/ZEN/A AGA TCA GTT TCC TAA TTC/3IABKFQ/(SEQ ID NO: 2), forward primer GGTTTTTCCTGTGGCTGAAAAAG (SEQ ID NO: 3) and reverse primer TGTCGGCAT-GAACCGTTCT (SEQ ID NO: 4). The wild type MET14-15 assay has probe/5HEX/CT ACT TTT C/ZEN/C AGA AGA TCA GTT TCC TAA T/3IABKFQ/(SEQ ID NO: 5) and primer of TGGTTTCAAATGAATCTGTAGACTA (SEQ ID NO: 6) and TGTCGGCATGAACCGTTCT (SEQ ID NO:4).

TABLE 1

Amplification results for mutant and wild type RT product as measured by ddPCR for the RT enzymes: PyroPhage ® 3173 DNA Polymerase, OmniAmp ™ DNA Polymerase and Tth DNA Polymerase.

| Enzyme | RT Cycles | Mutant Copies Expected | Mutant Copies Detected | Wild type Copies Detected | Mutant Fold Amplification |
|---|---|---|---|---|---|
| Tth | 1 | 240 | 0 | 16 | NA |
| Tth | 5 | 1200 | 2 | 19 | NA |
| Tth | 10 | 2400 | 0 | 10 | NA |
| Tth | 20 | 4800 | 0 | 53 | NA |
| PyroPhage ® | 1 | 240 | 237 | 779 | 1.0 |
| PyroPhage ® | 5 | 1200 | 59 | 477 | 0.2 |
| PyroPhage ® | 10 | 2400 | 42 | 895 | 0.2 |
| PyroPhage ® | 20 | 4800 | 46 | 960 | 0.2 |
| OmniAmp ™ | 1 | 240 | 239 | 3465 | 1.0 |
| OmniAmp ™ | 5 | 1200 | 638 | 6258 | 2.7 |
| OmniAmp ™ | 10 | 2400 | 8253 | Saturated | 34.4 |
| OmniAmp ™ | 20 | 4800 | Saturated | Saturated | NA |

The results for Example 1 are shown in Table 1. We detected OmniAmp™ amplification beyond the first cycle (equivalent to >100% conversion of the RNA template to cDNA). However, signal saturation was observed at higher cycles. OmniAmp™ Polymerase yielded 2.7 fold amplification of mutant MET with 5 cycles and 34.5 fold amplification at 10 RT cycles, but the signal was saturated by 10 RT cycles. Thus, the data indicated an initial stage of linear amplification followed by exponential amplification for OmniAmp™ Polymerase in this experiment. Since some signals were saturated and exceeded the instrument range for accurate quantification, the cDNA products from 20 cycles RT cycling generated by OmniAmp™ were diluted 100 to 1000 fold and re-analyzed on ddPCR.

TABLE 2

Copies of cDNA products measured by ddPCR for the diluted cDNA products of 20 amplification cycles using OmniAmp ™.

| Enzyme | RT Cycles | Dilution Factor | Mutant Copies Detected (dilution factor accounted) | Wild type Copies Detected (dilution factor accounted) |
|---|---|---|---|---|
| OmniAmp ™ | 20 | 100 | Saturated | Saturated |
| OmniAmp ™ | 20 | 1000 | 2520000 | 35196000 |

The results for the diluted cDNA products as shown in Table 2 indicate more than 10000 fold amplification at 20 cycles for OmniAmp™.

The results of Table 1 indicates that linear amplification with OmniAmp™ at lower RT cycles (e.g. about 1-5, compare data at 1, 5, and 10 cycles), however, the reaction conditions or the cycling protocol triggered exponential amplification at higher cycles (>5 cycles in this example). This could be due to non-specific priming, for example if significant RNA degradation during thermocycling results in the availability of short RNAs that can serve as (forward sense) primers for exponential amplification. RNA degradation at higher cycle numbers using temperatures as high as 95° C. in the presence of divalent metal ions would be consistent with the known lability of RNA via metal-activated hydrolysis.

Example 2: HawkZ05® DNA Polymerase and OmniAmp™ Using RNA Transcripts and Cell Line RNA This example evaluated whether OmniAmp™ DNA Polymerase and HawkZ05® Fast DNA Polymerase can amplify the RNA targets (mutant MET exon 13-15 fusion) from IVT RNA transcripts and cell-line wild type RNA (MET exon14-15 RNA) in reaction Buffer A (final concentration: 60 mM Tris-HCl, pH 8.4, 25 mM $(NH_4)_2SO_4$ and 10 mM KCl) using protocols with varied denaturation temperature and concentrations of Betaine (e.g., 80° C. with 2M Betaine or 95° C. with 1M Betaine).

The reactions were set up using mutant MET IVT in the background of wild type cell line RNA for 1 and 10 RT cycles and analyzed on ddPCR. The artificial mutant MET exon 13-15 fusion containing synthetic DNA template has the region of interest as: AGCACTGTTATTAC-TACTTGGGTTTTTCCTGTGGCT-GAAAAAGAGAAAGCAAAT TAAAGATCTGGGCAGT-GAATTAGTTCGCGCGATCGCTACGATGCAAGAGTA CA CACTCCTCATTTGGA-TAGGCTTGTAAGTGCCCGAAGTGTAAGCCCAACTA-CAGA AATGGTTTCAAATGAATCTGTAGAC-TACCGAGCTACTTTTCCAGAAGATCAGTT TCCTAATTCATCTCGCGATCGCAGAACGGTT-CATGCCGACAAGTGCAGTATCCT CTGACAGA-CATGTCCC (SEQ ID NO: 7). Foreign inserts of 7 bps were included into the artificial product (indicated in bold). The in vitro transcription products produced by T7 RNA polymerase were DNase treated, column purified and diluted to the proper concentration.

During the RT step, 1 to 30 cycles of primer annealing and extension on the RNA target were evaluated. The cycling conditions were one cycle of 68° C./1 min, 55° C./1 min, 68° C./2 min followed by 0, 4, 9, 19, and 29 cycles of 68° C./1 min, 80° C. or 95° C./15 sec, 68° C./2 min to achieve a total of 1, 5,10, 20, 30 cycles of RT. The RT reaction conditions were: 10 µl with Buffer A (60 mM Tris-HCl, pH 8.4, 25 mM $(NH_4)_2SO_4$ and 10 mM KCl), 200 µM dNTPs, 1 µM reverse primer. Divalent metal ion cofactor addition was 1 mM $Mg_2SO_4$ and 1 mM $Mn(OAc)_2$ for OmniAmp™ and HawkZ05® RT reactions, respectively.

Table 3 shows cDNA copies from mutant IVT transcript detected on ddPCR with OmniAmp™ and HawkZ05® Fast DNA Polymerase after 1, 5, 10, 20 and 30 RT cycles using Buffer A at 80° C./2 M Betaine conditions. The initial template amount added to the reactions was 500 copies of IVT mutant RNA transcripts (quantified by spectrophotometry) with or without approximately 10,000 copies (quantified by independent ddPCR assay) of wild type cell line RNA. After RT cycling, 20% of RT reactions by volume were transferred to ddPCR assays. Therefore, the theoretical copy number mutant MET input copies into ddPCR was 100 copies and wild type MET was approximately 2000 copies. With 5,10, 20 and 30 RT cycles, the theoretical detected mutant copies was expected to be approximately 5, 10, 20 and 30 fold more, assuming 100% efficiency and perfectly linear amplification via RT. For OmniAmp™, approximately 4, approximately 7, approximately 13, and approximately 18-fold amplification of the mutant copies were detected at 5, 10, 20, and 30 RT cycles, respectively. For the wild type MET, approximately 3, approximately 6, approximately 11 and approximately 15-fold amplification was detected at 5, 10, 20 and 30 cycles, respectively. Similar results were observed for the HawkZ05® enzyme. A more muted effect without background cell line RNA was observed. Thus, when the denaturing temperature was 80° C. using 2 M Betaine, rather than 95° C. and 1M Betaine (as shown below), the reaction supported up to 30 cycles of linear amplification. This is consistent with additional RNA stability studies that directly measured RNA degradation at 80° C. and 95° C. using different concentrations for Betaine in Example 3.

TABLE 3 cDNA copies from mutant MET detected on ddPCR after 1, 5, 10, 20 and 30 RT cycles for HawkZ05 ® Fast DNA Polymerase and OmniAmp ™ DNA Polymerase at 80° C./2M Betaine condition.

| Emzyme/ Template | Detected Copies of mutant MET13-15 | | | | | Fold change | | | |
|---|---|---|---|---|---|---|---|---|---|
| | 1 | 5 | 10 | 20 | 30 | 5 cycles/ 1 cycle | 10 cycles/ 1 cycle | 20 cycles/ 1 cycle | 30 cycles/ 1 cycle |
| OmniAMP ™_W cell RNA | 78 | 340 | 566 | 1124 | 1420 | 4.4 | 7.3 | 14.4 | 18.2 |
| OmniAMP ™_W/O cell RNA | 80 | 322 | 508 | 962 | 1400 | 4.0 | 6.4 | 12.0 | 17.5 |
| HawkZ05 ®_W cell RNA | 74 | 360 | 650 | 1084 | 1332 | 4.9 | 8.8 | 14.6 | 18.0 |
| HawkZ05 ®_W/O cell RNA | 114 | 286 | 394 | 530 | 518 | 2.5 | 3.5 | 4.6 | 4.5 |
| OmniAMP ™_W cell RNA | 1860 | 6560 | 11220 | 20080 | 27360 | 3.5 | 6.0 | 10.8 | 14.7 |
| HawkZ05 ®_W cell RNA | 1900 | 6180 | 11440 | 20360 | 28260 | 3.3 | 6.0 | 10.7 | 14.9 |

Table 4 shows the detected cDNA copies from mutant IVT transcript and wild type RNA by ddPCR after Omni-Amp™ and HawkZ05® Fast DNA Polymerase 1, 5, 10, 20 and 30 RT cycles using Buffer A at 95° C./1 M Betaine conditions. With 5, 10, 20, and 30 cycles of RT, the theoretical detected mutant copies will be 5, 10, 20 and 30 fold more, assuming 100% efficiency and perfectly linear amplification. However, with sample containing wild type RNA exponential amplification was observed at higher cycle counts, and linear amplification was detected up to 10 or 20 cycles. This result is consistent with the possibility of RNA degradation products being utilized to prime the cDNA at later cycles, resulting in pseudo-exponential amplification. Additionally, at lower cycle counts the linear amplification appears less efficient than at low denaturation temperatures. This finding is consistent with both the loss of template through RNA degradation and/or the reduction of enzyme activity following repeated exposures to 95° C.

TABLE 4 cDNA copies from mutant MET detected on ddPCR after 1, 5, 10, 20 and 30 RT cycles for HawkZ05 ® Fast DNA Polymerase and OmniAmp ™ DNA Polymerase at 95° C./1M Betaine condition.

| Enzyme/ Template | Detected Copies of mutant, MET13-15 | | | | | Fold change | | | |
|---|---|---|---|---|---|---|---|---|---|
| | 1 | 5 | 10 | 20 | 30 | 5 cycles/ 1 cycle | 10 cycles/ 1 cycle | 20 cycles/ 1 cycle | 30 cycles/ 1 cycle |
| OmniAMP ™_W cell RNA | 90 | 144 | 150 | 190 | 160 | 1.6 | 1.7 | 2.1 | 1.8 |
| OmniAMP ™_W/O cell RNA | 82 | 274 | 424 | 1080 | 6780 | 3.3 | 5.2 | 13.2 | 82.7 |
| HawkZ05 ®_W cell RNA | 106 | 382 | 582 | 882 | Saturated | 3.6 | 5.5 | 8.3 | Saturated |
| HawkZ05 ®_W/O cell RNA | 144 | 236 | 416 | 2580 | 12780 | 1.6 | 2.9 | 17.9 | 88.8 |

| | Detected Copies of wt MET14-15 | | | | | Fold change | | | |
|---|---|---|---|---|---|---|---|---|---|
| | 1 | 5 | 10 | 20 | 30 | 5 cycles/ 1 cycle | 10 cycles/ 1 cycle | 20 cycles/ 1 cycle | 30 cycles/ 1 cycle |
| OmniAMP ™_W cell RNA | 2100 | 5440 | 9960 | 18220 | Saturated | 2.6 | 4.7 | 8.7 | Saturated |
| HawkZ05 ®_W cell RNA | 2140 | 8120 | 14040 | Saturated | Saturated | 3.8 | 6.6 | Saturated | Saturated |

Example 3: Template (IVT) Fragmentation at 80° C. vs. 95° C.

To further determine whether high denaturation temperature (95° C.) results in RNA degradation associated with self-priming, reactions were set up using synthetic RNA of uniform length of mutant MET 13-15 IVT in Buffer A (final concentration: 60 mM Tri-HCl, pH 8.4, 25 mM $(NH_4)_2SO_4$, 10 mM KCl, and $MgSO_4$ at varying concentrations) with 1M betaine and 2M betaine and exposed to 1, 2, 5, 10, 20, 30 mins at 95° C. and 80° C., respectively. Following incubation, the RNA products were analyzed on an Agilent 2100 bioanalyzer using Agilent RNA 6000 Nano Kit.

In Buffer A, RNA was stable at 80° C. up to 30 mins while at 95° C., RNA is completely degraded after 10 mins (see, FIG. 1).

Example 4: HawkZ05® and OmniAmp™ Testing

This example was designed to test OmniAmp™ DNA Polymerase and HawkZ05® Fast DNA Polymerase (Roche Corp, Catalog No. 07 731 329 103) for the ability to perform linear amplification using single DNA primer in their respective manufacturing reaction buffer and Buffer A.

The manufacturer recommended protocol used in this experiment for OmniAmp™ enzyme included OmniAmp™ DNA Polymerase Buffer C with 2 mM $MgSO_4$, dNTPs at final concentration of 800 μM each, supplementation of 5 mM (final) $MgSO_4$, 1 μM reverse primer and 1× OmniAmp™ DNA Polymerase.

The manufacturer recommended protocol for HawkZ05® enzyme were set up using 1× final concentration of HawkZ05R DNA Polymerase 5× Master Mix (250 mM Tricine, 400-500 mM potassium acetate, 10-25% glycerol, 0.05% Tween 20, pH 8.0.), 1.5 mM (final) manganese acetate, dNTPs at 200 μM (final) each, 1 μM reverse primer and 10 U HawkZ05® Fast DNA Polymerase enzyme per 10 μL reaction.

For both enzymes, the reactions in Buffer A were done using 1 mM (final) $MgSO_4$ and 200 μM (final) dNTPs.

The experiment was set up using mutant MET IVT in the background of wild type cell line RNA for 1, 5 and 10 RT cycles at the following conditions: 95° C./1M Betaine and 80° C./2 M Betaine. The template and primer sequences are provided in Example 2. The cDNA products were analyzed using ddPCR assay for MET exon 14 skipping and wild type MET. The expected copies of mutant MET IVT in ddPCR was 260. This expected copy number is based on mathematical conversion of mass determined by spectrophotometric method (Nanodrop) to a theoretical copy number value. The mass transfer of wild type cell line cDNA into ddPCR was 1.2 ng.

As shown in Table 5, OmniAmp™ enzyme showed linear amplification of mutant MET IVT in Buffer A at 80° C./2 M Betaine condition. Amplification was poorer in OmniAmp™ buffer. More than 100% cDNA synthesis of mutant MET IVT was observed at both conditions: 95° C./1M Betaine and 80° C./2 M Betaine.

TABLE 5 cDNA copies from mutant IVTs detected on ddPCR for OmniAmp™ at 1, 5 and 10 RT cycles using manufactured reaction buffer and Buffer A at 95° C./1M Betaine and 80° C./2M Betaine conditions.

| Enzyme | Reaction conditions | Temp. (° C.) | Betaine final conc. (M) | 1 cycle Mutant copies detected | 5 cycles Mutant copies detected | 10 cycles Mutant copies detected | Fold change 5 cycles/ 1 cycle | Fold change 10 cycles/ 1 cycle |
|---|---|---|---|---|---|---|---|---|
| OmniAmp™ | Buffer A | 80 | 2 | 378 | 1356 | 2300 | 3.6 | 6.1 |
| OmniAmp™ | OmniAmp™ Buffer | 80 | 2 | 294 | 552 | 940 | 1.9 | 3.2 |
| OmniAmp™ | Buffer A | 95 | 1 | 426 | 1042 | 420 | 2.4 | 1.0 |
| OmniAmp™ | OxmniAmp™ Buffer | 95 | 1 | 336 | 928 | 1860 | 2.8 | 5.5 |

Results for wild type cell line cDNA copies as shown in Table 6 also showed linear amplification in Buffer A at 80° C./2 M Betaine condition. At 95° C./1 M Betaine condition in OmniAmp buffer, exponential amplification was observed at 10 cycles indicating potential priming from fragmented RNA.

TABLE 6

Background cell line RNA cDNA copies detected on ddPCR for OmniAmp™ at 1, 5 and 10 RT cycles using manufactured reaction buffer and Buffer A at 95° C./1M Betaine and 80° C./2M Betaine conditions.

| Enzyme | Reaction conditions | Temp. (° C.) | Betaine final conc (M) | 1 cycle Wild type copies detected | 5 cycles Wild type copies detected | 10 cycles Wild type copies detected | Fold change 5 cycles/ 1 cycle | Fold change 10 cycles/ 1 cycle |
|---|---|---|---|---|---|---|---|---|
| OmniAmp™ | Buffer A | 80 | 2 | 2080 | 8060 | 13400 | 3.9 | 6.4 |
| OmniAmp™ | OmniAmp™ Buffer | 80 | 2 | 2540 | 4280 | 5760 | 1.7 | 2.3 |
| OmniAmp™ | Buffer A | 95 | 1 | 1900 | 9240 | 7280 | 4.9 | 3.8 |
| OmniAmp™ | OmniAmp™ Buffer | 95 | 1 | 2480 | 11900 | 126400 | 4.8 | 51.0 |

HawkZ05® enzyme demonstrated more than 100% cDNA synthesis and linear amplification in HawkZ05® buffer for mutant MET IVT at 80° C./2M betaine condition (see, Table 7 below). The enzyme showed low amplification in Buffer A. As per manufacturer's protocol, HawkZ05® enzyme requires a manganese cation for RT activity. In this example Buffer A included $Mg^{2+}$ instead of $Mn^{2+}$.

TABLE 7 cDNA copies from mutant IVTs detected on ddPCR for HawkZ05 ® Fast DNA Polymerase at 1, 5 and 10 RT cycles using manufactured reaction buffer and Buffer A at 95° C./1M Betaine and 80° C./2M Betaine conditions.

| Enzyme | Reaction conditions | Temp. (° C.) | Betaine final conc (M) | 1 cycle Mutant copies detected | 5 cycles Mutant copies detected | 10 cycles Mutant copies detected | Fold change 5 cycles/ 1 cycle | Fold change 10 cycles/ 1 cycle |
|---|---|---|---|---|---|---|---|---|
| HawkZ05 ® | HawkZ05 ® buffer | 80 | 2 | 182 | 574 | 1120 | 3.2 | 6.2 |
| HawkZ05 ® | Buffer A | 80 | 2 | 11 | 34 | 56 | 3.1 | 5.1 |
| HawkZ05 ® | HawkZ05 ® buffer | 95 | 1 | 442 | 790 | 880 | 1.8 | 2.0 |
| HawkZ05 ® | Buffer A | 95 | 1 | 60 | 60 | 164 | 1.0 | 2.7 |

TABLE 8

Background cell line RNA cDNA copies detected on ddPCR for HawkZ05 ® Fast DNA Polymerase at 1, 5 and 10 RT cycles using manufactured reaction buffer and Buffer A at 95° C./1M Betaine and 80° C./2M Betaine conditions.

| Enzyme | Reaction conditions | Temp (° C.) | Betaine final conc (M) | 1 cycle Wild type copies detected | 5 cycles Wild type copies detected | 10 cycles Wild type copies detected | Fold change 5 cycles/ 1 cycle | Fold change 10 cycles/ 1 cycle |
|---|---|---|---|---|---|---|---|---|
| HawkZ05 ® | HawkZ05 ® buffer | 80 | 2 | 1590 | 4320 | 6060 | 2.7 | 3.8 |
| HawkZ05 ® | Buffer A | 80 | 2 | 76 | 166 | 220 | 2.2 | 2.9 |
| HawkZ05 ® | HawkZ05 ® buffer | 95 | 1 | 2740 | 9640 | 14120 | 3.5 | 5.2 |
| HawkZ05 ® | Buffer A | 95 | 1 | 736 | 1326 | 2140 | 1.8 | 2.9 |

These experiments demonstrate more than 100% cDNA synthesis and linear amplification using HawkZ05 Fast DNA Polymerase and OmniAmp™ DNA Polymerase.

Example 5: Tth DNA Polymerase, PyroPhage® 3173 DNA Polymerase and Wild Type Moloney Murine Leukemia Virus Reverse Transcriptase Enzyme Testing Tth DNA polymerase (Promega Corp, Part No. M210A) and PyroPhage® 3173 DNA Polymerase WT (Lucigen Corp, Catalog No. 30051-1) were evaluated for the ability to perform linear amplification at 1,5,10 and 20 RT cycle counts using a mixture of mutant MET IVT in the background of wild type cell line RNA at the more optimal 80° C./2M Betaine condition. In Example 1, Tth DNA polymerase and PyroPhage® 3173 DNA Polymerase Wild Type failed to demonstrate detectable linear RT amplification under the conditions evaluated. The reactions were set up using their respective manufactured buffers and Buffer A. In this experiment, alterations in the final reaction conditions (details provided below) were made to optimize these reactions relative to Example 1. In this experiment, reactions in Buffer A with a wild type Moloney Murine Leukemia Virus Reverse Transcriptase (MMLV RT) (Roche Corp, Catalog No. 04707486103) were also included. MMLV RT has optimal activity at 37-42° C. and would not be expect to demonstrate linear amplification using this method.

The manufacturer recommended protocol used for Pyro-Phage® 3173 DNA Polymerase was as follows: Pyro-Phage® 3173 PCR Buffer (Final concentration: 20 mM Tris-HCl, 10 mM (NH4)2SO4, 10 mM KCl, 2 mM MgSO4, 0.1% Triton X-100, thermoprotectant, pH 8.8 at 25° C.), dNTPs at a final concentration of 200 µM each, 1 µM reverse primer and 2.5 U of enzyme per 10 µL reaction.

For PyroPhage® 3173 DNA Polymerase WT and MMLV RT, reactions were set up in the Buffer A with 1 mM $Mg^{2+}$ and 2 mM $Mg^{2+}$ supplementation.

The manufacturer recommended protocol used for Tth enzyme was as follows: Tth RT buffer (Final concentration: 10 mM Tris-HCl, pH 8.3, 90 mM KCl), dNTPs at 200 µM each (final), 1 mM (final) MnCl2, 1 µM reverse primer and 5 U of enzyme per 10 µL reaction. Compared to Example 1, the enzyme units per reaction was increased by 5 fold in this experiment.

The concentrations of dNTPs, reverse primer and enzymes in reactions with Buffer A (final concentration: 60 mM Tri-HCl, pH 8.4, 25 mM $(NH_4)_2SO_4$, 10 mM KCl) were maintained same as the above protocols except for difference in the divalent cation used for the two enzymes. Since Tth DNA Polymerase requires $Mn^{2+}$ for RT activity, reactions in Buffer A using Tth DNA Polymerase were supplemented with 1 mM $MnCl_2$.

The amount of cDNA generated at 1, 5, 10 and 20 RT cycles were evaluated using ddPCR assay for MET exon 14 skipping and wild type MET. The expected number of copies of mutant MET IVT in ddPCR was 260. This expected copy number is based on mathematical conversion of mass determined by spectrophotometric method (Nanodrop) to a theoretical copy number value. The mass transfer of wild type cell line cDNA into ddPCR was 1.1 ng.

Results for mutant IVT and background cell line RNA indicate that Tth DNA Polymerase showed detectable linear amplification in both Tth buffer as well as in Buffer A up to at least 10 RT cycles. At higher cycles of 20, linear amplification of mutant IVT was well maintained in Buffer A. In Example 1, amplification using the Tth enzyme was not observed. In this experiment, the enzyme units were increased in the reaction and supplemented the reactions with Betaine. This resulted in efficient enzyme activity.

TABLE 9 cDNA copies from mutant IVTs detected on ddPCR for Tth DNA Polymerase, PyroPhage ® 3173 DNA Polymerase (wild type) and MMLV (wild type) RT Enzyme at 80° C./2M Betaine condition after 1,5, 10 and 20 RT cycles.

| Enzyme | Reaction condition | 1 cycle Mutant copies detected | 5 cycles Mutant copies detected | 10 cycles Mutant copies detected | 20 cycles Mutant copies detected | Fold change 5 cycles/ 1 cycle | Fold change 10 cycles/ 1 cycle | Fold change 20 cycles/ 1 cycle |
|---|---|---|---|---|---|---|---|---|
| Tth | Tth Buffer | 230 | 1082 | 2200 | 3100 | 4.7 | 9.6 | 13.5 |
| Tth | Tth Buffer | 272 | 1150 | 2360 | 3220 | 4.2 | 8.7 | 11.8 |
| Tth | Buffer A | 268 | 1050 | 2520 | 4160 | 3.9 | 9.4 | 15.5 |
| Tth | Buffer A | 278 | 1200 | 2420 | 4120 | 4.3 | 8.7 | 14.8 |
| PyroPhage ® | PyroPhage ® Buffer | 296 | 174 | 218 | | 0.6 | 0.7 | 0.7 |
| PyroPhage ® | PyroPhage ® Buffer | 300 | 200 | 226 | 276 | 0.7 | 0.8 | 0.9 |
| PyroPhage ® | Buffer A (1 mM $Mg^{2+}$) | 208 | 362 | 414 | 176 | 1.7 | 2.0 | 0.8 |
| PyroPhage ® | Buffer A (1 mM $Mg^{2+}$) | 208 | 410 | 358 | 142 | 2.0 | 1.7 | 0.7 |
| PyroPhage ® | Buffer A (2 mM $Mg^{2+}$) | 320 | 712 | 552 | 256 | 2.2 | 1.7 | 0.8 |
| PyroPhage ® | Buffer A (2 mM $Mg^{2+}$) | 308 | 810 | 592 | 292 | 2.6 | 1.9 | 0.9 |
| MMLV RT | Buffer A (1 mM $Mg^{2+}$) | 74 | 90 | 90 | 96 | 1.2 | 1.2 | 1.3 |
| MMLV RT | Buffer A (2 mM $Mg^{2+}$) | 106 | 96 | 92 | 110 | 0.9 | 0.9 | 1.0 |

TABLE 10

Background cell line RNA cDNA copies detected on ddPCR for Tth DNA Polymerase, PyroPhage ® 3173 DNA Polymerase and wild type MMLV RT enzyme using manufactured reaction buffer and Buffer A at 80° C./2M Betaine condition after 1, 5, 10 and 20 RT cycles.

| Enzyme | Reaction condition | 1 cycle Wild type Copies Detected | 5 cycles Wild type Copies Detected | 10 cycles Wild type Copies Detected | 20 cycles Wild type Copies Detected | Fold change 5 cycles/ 1 cycle | Fold change 10 cycles/ 1 cycle | Fold change 20 cycles/ 1 cycle |
|---|---|---|---|---|---|---|---|---|
| Tth | Tth Buffer | 1740 | 6340 | 13340 | 24340 | 3.6 | 7.7 | 14.0 |
| Tth | Tth Buffer | 1880 | 6560 | 13880 | 44500 | 3.5 | 7.4 | 23.7 |
| Tth | Buffer A | 1570 | 6600 | 14360 | 24780 | 4.2 | 9.1 | 15.8 |
| Tth | Buffer A | 1630 | 6340 | 13100 | 24420 | 3.9 | 8.0 | 15.0 |
| PyroPhage ® | PyroPhage ® Buffer | 2060 | 1100 | 962 | 1120 | 0.5 | 0.5 | 0.5 |
| PyroPhage ® | PyroPhage ® Buffer | 2040 | 1098 | 1030 | 1220 | 0.5 | 0.5 | 0.6 |
| PyroPhage ® | Buffer A (1 mM $Mg^{2+}$) | 936 | 2400 | 3860 | 3860 | 2.6 | 4.1 | 4.1 |
| PyroPhage ® | Buffer A (1 mM $Mg^{2+}$) | 900 | 2380 | 3360 | 4200 | 2.6 | 3.7 | 4.7 |
| PyroPhage ® | Buffer A (2 mM $Mg^{2+}$) | 2100 | 7840 | 12980 | 16720 | 3.7 | 6.2 | 8.0 |
| PyroPhage ® | Buffer A (2 mM $Mg^{2+}$) | 1960 | 8380 | 12700 | 16740 | 4.3 | 6.5 | 8.5 |
| MMLV | Buffer A (1 mM $Mg^{2+}$) | 288 | 246 | 274 | 310 | 0.9 | 1.0 | 1.1 |
| MMLV | Buffer A (2 mM $Mg^{2+}$) | 286 | 320 | 322 | 330 | 1.1 | 1.1 | 1.2 |

In the manufacturer recommended buffer, PyroPhage® 3173 DNA Polymerase showed amplification only at single cycle and linear amplification was clearly not observed. In Buffer A at 2 mM $Mg^{2+}$ concentrations, PyroPhage® 3173 DNA Polymerase showed signs of linear amplification up to 10 RT cycles as per results for background cell line cDNA copies shown in Table 10.

MMLV RT enzyme produced cDNA copy numbers that did not linearly increase with increasing cycle numbers, up to 20 RT cycles. Linear amplification was not observed using this thermolabile MMLV RT enzyme. In this experiment, it was demonstrated that at 80° C./2M Betaine condition in Buffer A, thermostable RT enzymes, Tth DNA Polymerase and PyroPhage® 3173 DNA Polymerase are capable of linear amplification whereas the thermolabile enzyme MMLV RT cannot perform linear amplification.

Example 6: Evaluating the Optimal Concentration of $Mg^{2+}$ for Linear Amplification In this example, a range of $Mg^{2+}$ concentrations were tested by varying the final reaction conditions from 0.5 mM to 10 mM and evaluating the amount of product generated at 1 and 10 RT cycles. OmniAmp™ polymerase was used with Buffer A. The dNTPs were included at a final concentration of 200 µM each. OmniAmp™ with its provided buffer at 2 mM $MgSO_4$ and high dNTP concentration (800 µM (final) each) was included as a control. 10× Buffer A was prepared without $MgSO_4$ and supplemented with a final concentration of 0.5, 1, 2, 5 or 10 mM $MgSO_4$.

The reverse primer for RT cycling has the sequence of TACTGCACTTGTCGGCATGAA (SEQ ID NO: 1). The digital PCR for mutant MET exon 13-15 fusion detection has the probe/primer pair sequence of/56-FAM/AG CAA ATT A/ZEN/A AGA TCA GTT TCC TAA TTC/3IABKFQ/ (SEQ ID NO: 2), forward primer GGTTTTTCCTGTGGCT-GAAAAAG (SEQ ID NO: 3) and reverse primer TGTCGG-CATGAACCGTTCT (SEQ ID NO: 4). The wild type MET14-15 assay has probe/5HEX/CT ACT TTT C/ZEN/C AGA AGA TCA GTT TCC TAA T/3IABKFQ/(SEQ ID NO: 5) and primer of TGGTTTCAAATGAATCTGTAGACTA (SEQ ID NO: 6) and TGTCGGCATGAACCGTTCT (SEQ ID NO: 4).

The expected number of copies of mutant MET IVT in ddPCR was 520. This expected copy number is based on mathematical conversion of mass determined by spectrophotometric method (Nanodrop) to a theoretical copy number value. The mass transfer of wild type cell line cDNA into ddPCR was 2.4 ng.

TABLE 11

Mutant copies of cDNA from IVT detected on ddPCR for OmniAmp ™ at varying concentrations of $Mg^{2+}$ in the RT reaction.

| $Mg^{2+}$ Concentration (mM) | Mutant Copies Detected 1 Cycle | Mutant Copies Detected 10 Cycles | Fold amplification |
| --- | --- | --- | --- |
| 0.5 | 342 | 114 | 0 |
| 1 | 582 | 1920 | 3 |
| 2 | 666 | 2620 | 4 |
| 5 | 614 | 3240 | 5 |
| 10 | 568 | 1900 | 3 |
| Original OmniAmp ™ Buffer(2 mM) | 560 | 1140 | 2 |

TABLE 12

Wild type cDNA copies from background Cell line RNA detected on ddPCR for OmniAmp ™ at varying concentrations of $Mg^{2+}$ in the RT reaction.

| $Mg^{2+}$ Concentration (mM) | Wild type Copies Detected 1 Cycle | Wild type Copies Detected 10 Cycles | Fold amplification |
| --- | --- | --- | --- |
| 0.5 | 2660 | 1520 | 1 |
| 1 | 3060 | 22200 | 7 |
| 2 | 3980 | 21000 | 5 |
| 5 | 4100 | 8300 | 2 |
| 10 | 3000 | 4540 | 2 |
| Original OmniAmp ™ Buffer(2 mM) | 4340 | 2720 | 1 |

In this experiment, the OmniAmp™ enzyme did not manifest linear amplification in its original buffer with 2 mM $Mg^{2+}$ concentration as shown in Table 11 and Table 12. However, appreciable amplification was observed using Buffer A, with an optimum approximately 1-2 mM $Mg^{2+}$.

Example 7: $Mn^{2+}$ Suitability Testing

In this example the suitability of $Mn^{2+}$ instead of $Mg^{2+}$ was assessed to determine if and how $Mn^{2+}$ substitution impacts linear amplification. OmniAmp™ Polymerase was tested using Buffer A without $MgSO_4$ as prepared above. The dNTPs were included at a final concentration of 200 µM each. Reaction addition of $MnCl_2$ was done targeting 0.5, 1, 2, 5 and 10 mM final concentration. The reactions were set up using gBlock mutant MET IVT in the background of wild type cell line RNA for 1 and 10 RT cycles and analyzed on ddPCR. The expected copy number of mutant MET IVT in ddPCR was 520. This expected copy number is based on mathematical conversion of mass determined by spectrophotometric method (Nanodrop) to a theoretical copy number value. 12 ng of wild type cell line RNA was added to 10 µL RT reaction. 20% of cDNA products were transferred to ddPCR assay. The mass transfer of wild type cell line cDNA into ddPCR was 2.4 ng.

TABLE 13

Copies of cDNA from IVT mutant detected on ddPCR for OmniAmp ™ at 1 and 10 RT cycles using varying concentrations of manganese.

| $Mn^{2+}$ Concentration (mM) | Mutant Copies Detected 1 Cycle | Mutant Copies Detected 10 Cycles | Fold amplification |
| --- | --- | --- | --- |
| 0.5 | 588 | 2840 | 5 |
| 1 | 496 | 1640 | 3 |
| 2 | 476 | 1200 | 3 |
| 5 | 526 | 280 | 1 |
| 10 | 502 | 380 | 1 |

TABLE 14

Copies of cDNA from wild type cell line RNA copies detected on ddPCR for OmniAmp ™ at 1 and 10 RT cycles using varying concentrations of $Mn^{2+}$.

| $Mn^{2+}$ Concentration (mM) | Wild type Copies Detected 1 Cycle | Wild type Copies Detected 10 Cycles | Fold amplification |
|---|---|---|---|
| 0.5 | 3800 | 17000 | 4 |
| 1 | 4000 | 11480 | 3 |
| 2 | 4320 | 9220 | 2 |
| 5 | 4300 | 6140 | 1 |
| 10 | 3940 | 3900 | 1 |

Figure 2:
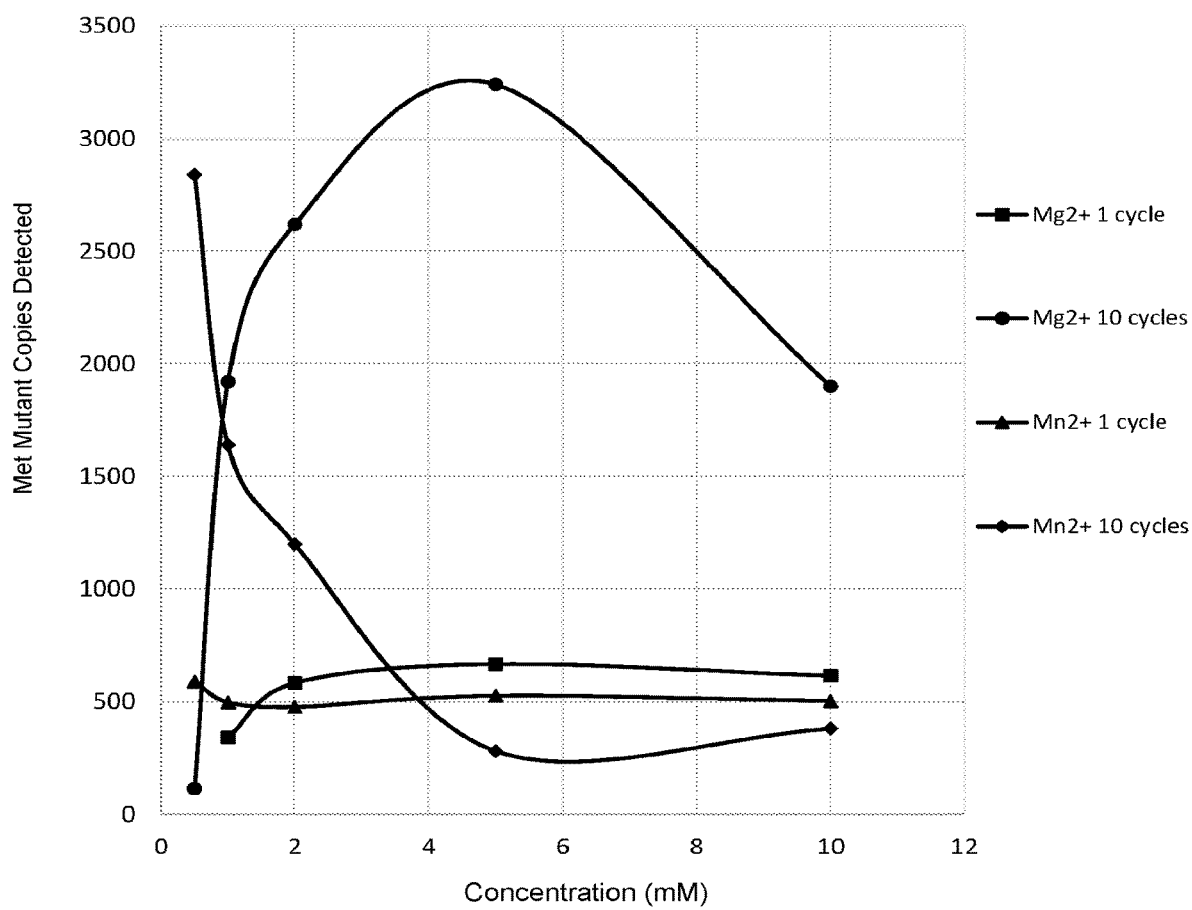
FIG. 2 Depicts the effect of concentration of manganese and magnesium on mutant MET IVT amplification using OmniAmp™ at 1 and 10 reverse transcriptase cycles.

Comparison of results for concentration effect of $Mn^{2+}$ on linear amplification to the results of experiment 2 using $Mg^{2+}$ for OmniAmp™ showed that at 10 cycles, with increasing $Mn^{2+}$, linear amplification decreased significantly. Fold amplification between 1 and 10 cycles was non-linear for the targets using either of the divalent ions as seen in FIG. 2. In the tested range, OmniAmp™ enzyme showed better tolerance to $Mg^{2+}$ compared to $Mn^{2+}$. In this experiment, the results indicate that $Mn^{2+}$ concentrations significantly decrease the ability of OmniAmp™ to perform linear amplification. OmniAmp™ shows better tolerance to $Mg^{2+}$ compared to $Mn^{2+}$.

Example 8: Concentration of $Mn^{2+}$ in Linear Amplification by HawkZ05® Fast DNA Polymerase Example 8 evaluated the concentration of $Mn^{2+}$ required for linear amplification by HawkZ05® Fast DNA Polymerase in HawkZ05® buffer condition and Buffer A using single DNA primer. The manufacturer recommended protocol for HawkZ05® enzyme was set up using 1× final concentration of HawkZ05® DNA Polymerase 5× Master Mix (250 mM Tricine, 400-500 mM potassium acetate, 10-25% glycerol, 0.05% Tween 20, pH 8.0.), dNTPs at 200 µM (final) each, 1 µM reverse primer, varying manganese concentration and 10 U HawkZ05® Fast DNA Polymerase enzyme per 10 µL reaction. The reactions in Buffer A (final concentration: 60 mM Tri-HCl, pH 8.4, 25 mM $(NH_4)_2SO_4$, 10 mM KCl) were also set up using dNTPs at 200 µM (final) each, 1 µM reverse primer, varying manganese concentrations and 10 U HawkZ05® Fast DNA Polymerase enzyme per 10 µL reaction. The concentrations of manganese tested in this experiment were 1 mM, 2 mM and 3 mM.

The RT cycling was set up using mutant MET IVT in the background of wild type cell line RNA for 1, 5 and 10 RT cycles at 80° C./2 M Betaine condition. The amount of cDNA generated at 1, 5 and 10 RT cycles were evaluated using ddPCR assay for MET exon 14 skipping and wild type MET. The expected copies of mutant MET IVT in ddPCR was 260. This expected copy no. is based on mathematical conversion of mass determined by spectrophotometric method (Nanodrop) to a theoretical copy number value. The mass transfer of wild type cell line cDNA into ddPCR was 1.1 ng.

TABLE 15 cDNA copies from mutant IVTs detected on ddPCR for HawkZ05 ® Fast DNA Polymerase at varying concentrations of manganese using manufactured reaction buffer and Buffer A at 80° C./2M Betaine condition after 1, 5 and 10 RT cycles.

| Reaction conditions | Mn2+ concentration (mM) | 1 cycle Mutant copies detected | 5 cycles Mutant copies detected | 10 cycles Mutant copies detected | Fold change 5 cycles/ 1 cycle | Fold change 10 cycles/ 1 cycle |
|---|---|---|---|---|---|---|
| HawkZ05 ® buffer | 1 | 208 | 642 | 860 | 3.1 | 4.1 |
| HawkZ05 ® buffer | 2 | 296 | 832 | 940 | 2.8 | 3.2 |
| HawkZ05 ® buffer | 3 | 306 | 826 | 620 | 2.7 | 2.0 |
| Buffer A | 1 | 422 | 1660 | 2940 | 3.9 | 7.0 |
| Buffer A | 2 | 380 | 1300 | 1240 | 3.4 | 3.3 |
| Buffer A | 3 | 372 | 954 | 640 | 2.6 | 1.7 |

As seen in Table 15 and 16, 1 mM $Mn^{2+}$ concentration was preferred for linear amplification of mutant IVT and wild type background up to 5 cycles in HawkZ05® buffer. However, linear amplification was affected at 10 cycles in Hawkz05® buffer. Comparatively, HawZ05 Fast DNA polymerase performed better in Buffer A at 1 mM $Mn^{2+}$ concentration yielding close to 4 fold amplification of mutant IVT at 5 cycles and 7 fold amplification at 10 cycles. In example 4, poor amplification was observed in Buffer A in the absence of $Mn^{2+}$. Here, supplementation of $Mn^{2+}$ in the Buffer A increased the amplification efficiency.

TABLE 16

Background cell line RNA cDNA copies detected on ddPCR for HawkZ05 ® Fast DNA Polymerase at varying concentrations of manganese using manufactured reaction buffer and Buffer A at 80° C./2M Betaine condition after 1, 5 and 10 RT cycles.

| Reaction conditions | Mn2+ concentration (mM) | 1 cycle Wild type copies detected | 5 cycles Wild type copies detected | 10 cycles Wild type copies detected | Fold change 5 cycles/ 1 cycle | Fold change 10 cycles/ 1 cycle |
|---|---|---|---|---|---|---|
| HawkZ05 ® buffer | 1 | 1440 | 4120 | 5320 | 2.9 | 3.7 |
| HawkZ05 ® buffer | 2 | 2060 | 4940 | 3080 | 2.4 | 1.5 |
| HawkZ05 ® buffer | 3 | 1920 | 4880 | 2660 | 2.5 | 1.4 |
| Buffer A | 1 | 2260 | 7460 | 8560 | 3.3 | 3.8 |
| Buffer A | 2 | 2140 | 6780 | 3140 | 3.2 | 1.5 |
| Buffer A | 3 | 2020 | 5500 | 1760 | 2.7 | 0.9 |

Here HawkZ05® Fast DNA Polymerase was capable of linear amplification in Buffer A in the presence of 1 mM $Mn^{2+}$ at 80° C./2M Betaine condition.

Example 9: RT Linear Amplification from RNA Derived from FFPE Tissue

In this example, the HawkZ05® Fast DNA Polymerase and OmniAmp™ DNA Polymerase were evaluated for their ability to perform linear amplification using RNA isolated from a MET mutant (30% MET exon 14 skipped) FFPE sample.

The reactions in Buffer A were set up with difference in the divalent cation used for the two enzymes. For OmniAmp™ DNA Polymerase, Buffer A was supplemented with 1 mM $MgCl_2$. For HawkZ05® Fast DNA Polymerase, Buffer A was supplemented with 1 mM $MnCl_2$. The concentrations of dNTPs, reverse primer and enzyme units were same as Example 4. The FFPE sample was titrated at three concentration inputs into RT reactions: 5.6 ng, 0.56 ng and 0.28 ng. RT cycling was done at 80° C./2M Betaine condition for 1, 5, 10 and 20 cycles.

The amount of cDNA generated at 1, 5, 10 and 20 RT cycles were evaluated using ddPCR assay for MET exon 14 skipping and wild type MET.

TABLE 17 cDNA copies from mutant MET detected on ddPCR after 1, 5, 10 and 20 RT cycles for HawkZ05 ® Fast DNA Polymerase and OmniAmp ™ DNA Polymerase using different concentrations of FFPE.

| Enzyme | FFPE ng input into RT | Met 13-15 copies into RT | Met 13-15 Copies transferred to ddPCR in 1 cycle | 1 cycle Mutant copies detected | 5 cycles Mutant copies detected | 10 cycles Mutant copies detected | 20 cycles Mutant copies detected | Fold change 5 cycles/ 1 cycle | Fold change 10 cycles/ 1 cycle | Fold change 20 cycles/ 1 cycle |
|---|---|---|---|---|---|---|---|---|---|---|
| HawkZ05 ® | 5.6 ng | 270 | 54 | 44 | 174 | 316 | 406 | 4.0 | 7.2 | 9.2 |
| HawkZ05 ® | 0.56 ng | 27 | 5.4 | 5.8 | 15 | 22 | 26 | 2.6 | 3.8 | 4.5 |
| HawkZ05 ® | 0.28 ng | 13.5 | 2.7 | 4 | 8.6 | 16 | 13.4 | 2.2 | 4.0 | 3.4 |
| OmniAmp ™ | 5.6 ng | 270 | 54 | 56 | 184 | 308 | 370 | 3.3 | 5.5 | 6.6 |
| OmniAmp ™ | 0.56 ng | 27 | 5.4 | 6 | 20 | 34 | 48 | 3.3 | 5.7 | 8.0 |
| OmniAmp ™ | 0.28 ng | 13.5 | 2.7 | 2.8 | 10 | 12.2 | 38 | 3.6 | 4.4 | 13.6 |

TABLE 18

Copies of wild type MET detected on ddPCR after 1, 5, 10 and 20 RT cycles for HawkZ05 ® Fast DNA Polymerase and OmniAmp ™ DNA Polymerase using different concentrations of FFPE.

| Enzyme | FFPE ng input into RT | 1 cycle Wild type Met 14-15 copies detected | 5 cycles Wild type Met 14-15 copies detected | 10 cycles Wild type Met 14-15 copies detected | 20 cycles Wild type Met 14-15 copies detected | Fold change 5 cycles/ 1 cycle | Fold change 10 cycles/ 1 cycle | Fold change 20 cycles/ 1 cycle |
|---|---|---|---|---|---|---|---|---|
| HawkZ05 ® | 5.6 ng | 124 | 424 | 638 | 738 | 3.4 | 5.1 | 6.0 |
| HawkZ05 ® | 0.56 ng | 24 | 32 | 56 | 88 | 1.3 | 2.3 | 3.7 |
| HawkZ05 ® | 0.28 ng | 9.4 | 22 | 18 | 46 | 2.3 | 1.9 | 4.9 |
| OmniAmp ™ | 5.6 ng | 88 | 304 | 568 | 690 | 3.5 | 6.5 | 7.8 |
| OmniAmp ™ | 0.56 ng | 13.6 | 52 | 66 | 166 | 3.8 | 4.9 | 12.2 |
| OmniAmp ™ | 0.28 ng | 5.6 | 34 | 32 | 58 | 6.1 | 5.7 | 10.4 |

Results indicate more than 100% cDNA synthesis using FFPE samples by both enzymes tested. Linear amplification was observed to at least 5-10 RT cycles in all the reactions. Although the reaction efficiency dropped off at 20 cycles for both mutant copies as well as wild type, the fraction variant (~30%) as shown in Table 17 was well preserved up to 20 RT cycles.

TABLE 19

Fraction of mutant variant detected on ddPCR after 1, 5, 10 and 20 RT cycles.

| Enzyme | FFPE ng input into RT | 1 cycle % variant detected | 5 cycles % variant detected | 10 cycles % variant detected | 20 cycles % variant detected |
|---|---|---|---|---|---|
| HawkZ05 ® | 5.6 ng | 26 | 29 | 33 | 35 |
| HawkZ05 ® | 0.56 ng | 19 | 32 | 28 | 23 |
| HawkZ05 ® | 0.28 ng | 30 | 28 | 47 | 23 |
| OmniAmp ™ | 5.6 ng | 39 | 38 | 35 | 35 |
| OmniAmp ™ | 0.56 ng | 31 | 28 | 34 | 22 |
| OmniAmp ™ | 0.28 ng | 33 | 23 | 28 | 40 |

In this example, it was demonstrated that more than 100% cDNA synthesis is achievable using FFPE RNA and this sample type is compatible with linear amplification in Buffer A at 80° C./2M Betaine condition using thermostable RT enzymes HawkZ05® Fast DNA Polymerase and Omni-Amp™ DNA Polymerase.

The invention claimed is:

1. A kit for improving cDNA synthesis by linear amplification of an RNA template, said kit comprising:
   a reaction volume containing buffer, dNTPs, betaine or a betaine analog in an amount of about 0.75 to about 3.5 M, and a first primer complementary to an RNA template; and
   a thermostable reverse transcriptase capable of synthesizing cDNA by linear amplification of the RNA template;
   wherein at least one cycle of cDNA synthesis includes an extension temperature and a denaturation temperature; and
   wherein the denaturation temperature is about 75 degrees C. to 90 degrees C.

2. The kit of claim 1, wherein the kit does not comprise a functional primer capable of amplifying the synthesized cDNA.

3. The kit of claim 1, wherein the kit further comprises a functional second primer that is complementary to the cDNA and capable of amplifying the cDNA.

4. The kit of claim 1, wherein the kit further comprises one or more nonfunctional primers that are complementary to the cDNA and that can be functionalized to allow amplification of the cDNA.

5. The kit of claim 1, further comprising instructions for using the kit to synthesize cDNA.

6. The kit of claim 1, wherein the betaine analog is selected from homodeanol betaine, deanol betaine, propio betaine, homoglycerol betaine, diethanol homobetaine, triethanol homobetaine, hydroxypropyl homobetaine, N-Methyl-N-(2-carboxyethyl)morpholinium inner salt, N-Methyl-N-(2-carboxyethyl)piperidinium inner salt, N-Methyl-N-(2-carboxyethyl)pyrrolidinium inner salt, N,N-dimethyl-N-(2-hydroxyethyl)-N-(2-sulfoethyl)ammonium inner salt, N,N-dimethyl-N-(2-hydroxyethyl)-N-(3-sulfopropyl)ammonium inner salt, N,N-dihydroxyethyl-N-methyl-N-(3-sulfopropyl)ammonium inner salt, N,N-dimethyl-N-(2-hydroxyethyl)-N-(4-sulfobutyl)ammonium inner salt, N-methyl-N-(3-sulfopropyl)morpholinium inner salt, and N-methyl-N-(3-sulfopropyl)piperidium inner salt.

7. The kit of claim 1, wherein the betaine or betaine analog is at a concentration of at least or about 1-3 M.

8. The kit of claim 1, wherein the reaction volume further comprises $Mg^{2+}$ at a concentration of about 0.2-20 mM.

9. The kit of claim 8, wherein the $Mg^{2+}$ concentration is about 0.5-10 mM.

10. The kit of claim 1, wherein the thermostable reverse transcriptase does not have one or more activities selected from a 3' to 5' exonuclease activity, RNAse H activity, and strand displacement activity.

11. The kit of claim 1, wherein the kit further comprises at least a second primer in the reaction volume.

12. The kit of claim 1, wherein the thermostable reverse transcriptase is capable of synthesizing cDNA with denaturation times of 15 to 45 seconds per cycle.

13. The kit of claim 1, wherein the reaction volume further comprises 60 mM Tris-HCl, pH 8.4, 25 mM $(NH_4)_2SO_4$, and 10 mM KCl (Buffer A).

14. The kit of claim 1, wherein the denaturation temperature is about 75 degrees C. to about 80 degrees C. and the betaine is at about 2 M to about 3 M.

15. The kit of claim 1, wherein the denaturation temperature is about 80 degrees C. to about 85 degrees C. and the betaine is at about 1 M to about 2 M.

16. The kit of claim 1, wherein the thermostable reverse transcriptase is an error-correcting reverse transcriptase.

17. The kit of claim 1, wherein the thermostable reverse transcriptase comprises at least one proofreading domain.

18. The kit of any preceding claim, wherein the thermostable reverse transcriptase is selected from a retroviral reverse transcriptase, a family A DNA polymerase with reverse transcriptase activity, a family B DNA polymerase with reverse transcriptase activity, or a modified, mutated, or engineered variation thereof.

19. The kit of claim 1, further comprising an RNA template.

20. The kit of claim 19, wherein the RNA template is from a biological sample, wherein the biological sample is a FFPE, FNA, or biofluid sample.

21. The kit of claim 19, wherein the RNA template is a low-abundance RNA or an oncogene RNA.

22. The kit of claim 19, wherein the RNA template is a synthetic RNA template.

23. The kit according to any one of claims 19-22, wherein the RNA template is capable of undergoing 2-100 cycles of cDNA synthesis.

* * * * *

SEQUENCE LISTING

```
<160> NUMBER OF SEQ ID NOS: 7

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tactgcactt gtcggcatga a                                              21

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
aagatcagtt tcctaattc                                                 19

<210> SEQ ID NO 3
<211> LENGTH: 23
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 3 ggttttcct gtggctgaaa aag                                             23

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tgtcggcatg aaccgttct                                                 19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
cagaagatca gtttcctaat                                                20

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tggtttcaaa tgaatctgta gacta                                          25

<210> SEQ ID NO 7
<211> LENGTH: 285
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
agcactgtta ttactacttg ggttttcct gtggctgaaa agagaaagc aaattaaaga      60 tctgggcagt gaattagttc gcgcgatcgc tacgatgcaa gagtacacac tcctcatttg   120
gataggcttg taagtgcccg aagtgtaagc ccaactacag aaatggtttc aaatgaatct   180
gtagactacc gagctacttt tccagaagat cagtttccta attcatctcg cgatcgcaga   240
acggttcatg ccgacaagtg cagtatcctc tgacagacat gtccc                  285
```